(12) United States Patent
Joo et al.

(10) Patent No.: US 6,340,694 B1
(45) Date of Patent: Jan. 22, 2002

(54) DIARYLBENZOPYRAN DERIVATIVES AS CYCLOOXYGENASE-2 INHIBITORS

(75) Inventors: Yung Hyup Joo, Seoul; Chang Hoon Lee, Kyunggi-do; Min-Soo Noh, Seoul; Jun-Yong Ha, Kyunggi-do; Jin Kyu Choi; Kyung Min Lim, both of Suwon-si; Jin Kwan Kim; Seon-Hwa Kang, both of Seoul, all of (KR)

(73) Assignee: Pacific Corporation, Seoul (KR)

( * ) Notice: Subject to any disclaimer, the term of this patent is extended or adjusted under 35 U.S.C. 154(b) by 0 days.

(21) Appl. No.: 09/763,146

(22) PCT Filed: Aug. 20, 1999

(86) PCT No.: PCT/KR99/00469

§ 371 Date: Feb. 20, 2001

§ 102(e) Date: Feb. 20, 2001

(87) PCT Pub. No.: WO00/10993

PCT Pub. Date: Mar. 2, 2000

(30) Foreign Application Priority Data

Aug. 22, 1998 (KR) .............................. 98-34131

(51) Int. Cl.$^7$ .................. A61K 31/4433; A61K 31/352; C07D 405/04; C07D 407/04; C07D 409/04; C07D 417/04
(52) U.S. Cl. .................. 514/337; 514/255.05; 514/365; 514/374; 514/406; 514/443; 514/444; 514/456; 544/405; 546/283.1; 548/235; 548/203; 548/364.4; 549/58; 549/60; 549/401
(58) Field of Search .......................... 549/401, 58, 60; 548/235, 203, 364.4; 546/283.1; 544/405; 514/456, 337, 443, 444, 365, 406, 255.05, 374

(56) References Cited

U.S. PATENT DOCUMENTS 3,844,792 A * 10/1974 Zweig ......................... 96/90

FOREIGN PATENT DOCUMENTS

| WO | WO 96/06840 | * 3/1996 |
| WO | WO 96/13500 | 5/1996 |

OTHER PUBLICATIONS

27–Heterocyclic Compounds, vol. 68, 87102k.
J. R. Vane et al., Annu. Rev. Pharmacol. Toxicol. 1998. 38: 97–120.
Jeffery S. Carter, Exp. Opin. Ther. Patent (2000O 10(7), pp. 1011–1020.
Petpiboon Prasit and Denis Riendeau, Annual Reports in Medicinal Chemistry (1997), Chapter 21, pp. 211–220.
J. C. Frö lich. TiPS–Jan. 1997, vol. 18. pp. 30–34.
David DeWitt and William L. Smith, Cell, vol. 83, pp. 345–348, Nov. 3, 1995.
William L. Smith et al., The Journal of Biological Chemistry, vol. 271, No. 52, Issue of Dec. 27, pp. 33157–33160, 1996.
John Vane, Nature, vol. 367, Jan. 20, 1994.
Horng–Chih Huang et al., Bioorganic & Medicinal Chemistry Letters, vol. 5, No. 20, pp. 2377–2380, 1995.
W. C. Black et al., Bioorganic & Medicinal Chemistry Letters, vol. 6, No. 6, pp. 725–730, 1996.
Donald J. P. Pinto et al., Bioorganic & Medicinal Chemistry Letters, vol. 6, No. 24, pp. 2907–2912, 1996.
Horng–Chih Huang et al., J. Med. Chem. 1996, 39, pp. 253–266.
James J. Li et al., J. Med. Chem. 1996, 39, pp. 1846–1856.
Edward S. Lazer et al., J. Med Chem. 1997, 40, pp. 980–989.
Thomas D. Penning et al., J. Med. Chem. 1997, 40, pp. 1347–1365.
Thomas D. Penning et al., Bioorganic & Medicinal Chemistry Letters, vol. 7, No. 16, pp. 2121–2124, 1997.
Edward S. Lazer et al., Bioorganic & Medicinal Chemistry Letters 8 (1998), pp. 1181–1186.
Richard W. Friesen et al., Bioorganic & Medicinal Chemistry Letters 8 (1998), pp. 2777–2782.
Chun–Sing Li et al., Bioorganic & Medicinal Chemistry Letters 9 (1999), pp. 3181–3186.
Cheuk K. Lau et al all, Bioorganic & Medicinal Chemistry Letters 9 (1999), pp. 3187–3192.
Gerd Dannhardt et al., Eur. J. Med. Chem. 35 (2000), pp. 499–510.
Joan Bosch et all, Bioorganic & Medicinal Chemistry Letters 10 (2000), pp. 1745–1748.
Ish K. Khanna et al., J. Med. Chem. 2000, 43, pp. 3168–3185.
K. L. Prasunamba et al., Indian J. Chem., vol. 15B, Aug. 1997, pp. 756–758.
Barend C. B. Bezuidenhoudt et al., J. Chem. Soc. Perkin Trans. I. 1988, pp. 1227–1235.
K. Tanaka et al., Jpn. J. Pharmacol. 67, pp. 305–314 (1995).

* cited by examiner

*Primary Examiner*—Evelyn Mei Huang
(74) *Attorney, Agent, or Firm*—Finnegan, Henderson, Farabow, Garrett & Dunner LLP

(57) ABSTRACT

The diarylbenzopyran derivatives represented by formula I, and the pharmaceutically acceptable salts thereof, are disclosed. The composition comprising the compound of formula I, or a pharmaceutically acceptable salt thereof, shows an excellent selective inhibition of cyclooxygenase-2.

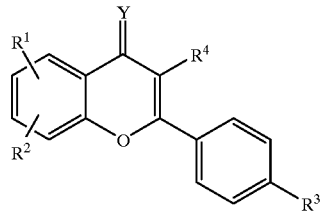

(I)

6 Claims, No Drawings

DIARYLBENZOPYRAN DERIVATIVES AS CYCLOOXYGENASE-2 INHIBITORS

This application is the national phase of PCT/KR99/00469 filed on Aug. 20, 1999.

BACKGROUND OF THE INVENTION

1. Field of the Invention

The present invention relates to diarylbenzopyran derivatives or their pharmaceutically acceptable salts and cyclooxygenase-2 inhibitor composition containing same.

2. Description of the Related Arts

Non-steroidal, antiinflammatory drugs(NSAIDs), which have been most prevalently used all over the world, have a problem of causing serious side-effects such as gastrointestinal tract or nephro-toxicity. NSAIDs inhibit the activity of cyclooxygenase(hereinafter "COX"), which is an enzyme involved in prostagladin synthesis, resulting in the inhibition of the biosynthesis of prostaglandin not only in inflammatory loci but also in stomach and kidney. It has been found that COX exists in the form of isoenzymes: COX-1 and COX-2[Cell, 83,345, (1995)]. COX-1 exists in normal cells and keeps cell homeostasis and controls the function of stomach and kidney, while COX-2 is expressed by mitogens or cytokines in pain sites where inflammation and other imrunoreactions occur [J. Biol. Chem., 271,33157(1996)] and is involved in pathologic phenomenon. Therefore the toxicity of NSAIDs is due to its inhibition of the coexisting COX-1's.

To avoid this problem, selective inhibitors of COX-2 has been investigated [Nature, 367, 215(1995)]. The selective inhibitors (i) have suitable antiinflammation, pain-relieving action, antipyretic action; (ii) remove toxicity from and reduce bleeding time in gastrointestinal tract and kidney; (iii) show potential anticancer activity and reduce the induction of mechanism-related side-effect; and also (iv) lower the induction of asthma in asthmatic patients who are sensitive to conventional NSAIDs. These selective inhibitors of COX-2 also show inhibition effect on smooth muscle constriction and could be used in treating Alzheimer's disease and osteoporosis of women after menopausa.

Active researches have been made on the selective inhibitors of COX-2. For example, WO 9606840, Bioorg, Med. Chem. Lett. 5, 2377(1995), Ann. Report. Med. Chem., 211(1997) and many other publications report COX-2 inhibitors having heterocyclic moiety as a base structure.

The present inventors made extensive researches to provide a new compound capable of inhibiting the COX-2's action selectively and strongly, and as a result found out that the diarylbenzopyran derivatives fulfill the requirements.

SUMMARY OF THE INVENTION

Therefore, an object of the present invention is to provide diarylbenzopyran derivatives represented by the following general formula (I):

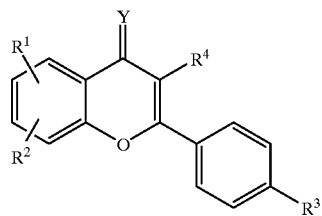

wherein

Y is an oxygen atom or a sulfur atom;

$R^1$ and $R^2$, identical to or different from each other, are independently a hydrogen atom, a halogen atom, a $C_1$–$C_6$ lower alkyl group, a trifluoromethyl group, an alkoxy group, a hydroxy group, a nitro group, a nitrile group, or a carboxyl group;

$R^3$ is a group of a formula: $S(O)nR^5$ wherein n is an integer of 0~2, $R^5$ is a hydrogen atom, a $C_1$–$C_6$ lower alkyl group, or a group of a formula: $NR^6R^7$ wherein $R^6$ and $R^7$, identical to or different from each other, are independently a hydrogen atom, or a $C_1$–$C_6$ lower alkyl group; and $R^4$ is oxazolyl, benzo[b]thienyl, furanyl, thienyl, naphthyl, thiazolyl, indolyl, pyrolyl, benzofuranyl, pyrazolyl, pyrazolyl substituted with a $C_1$–$C_6$ lower alkyl group, indanyl, pyrazinyl, or a substituted group presented by the following structures:

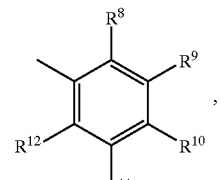

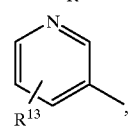

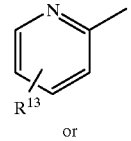

or

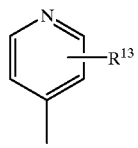

wherein $R^8$ through $R^{12}$, identical to or different from one another, are independently a hydrogen atom, a halogen atom, a $C_1$–$C_6$ lower alkyl group, a trifluoromethyl group, an alkoxy group, a hydroxy group, a hydroxyalkyl group, a nitro group, a group of a formula: $S(O)nR^{5'}$ a group of a formula: $NR^6R^7$, a trifluoromethoxy group, a nitrile group a carboxyl group, an acetyl group, or a formyl group, wherein n, $R^5$, $R^6$ and $R^7$ have the same meaning as defined by $R^3$ above; and $R^{13}$ is a hydrogen atom, a halogen atom, A $C_1$–$C_6$ lower alkyl group, a trifluoromethyl group, an alkoxy group, a hydroxy group, a trifluoromethoxy group, a carboxyl group, or an acetyl group;

Another object of the present invention is to provide a cyclooxygenase-2-inhibitor-composition comprising an effective amount of a compound represented by the above general formula(I) or a pharmaceutically acceptable salt thereof.

DETAILED DESCRIPTION OF THE INVENTION

The diarylbenzopyran derivatives or their pharmaceutically acceptable salts of the present invention effectively and selectively inhibit COX-2's action of biosynthesizing the prostagladin, which plays a more important role in progress of inflammation than COX-1.

The diarylbenzopyran derivatives of the present invention, which are useful as selective COX-2's inhibitor drugs, are represented by the following general formula(I)

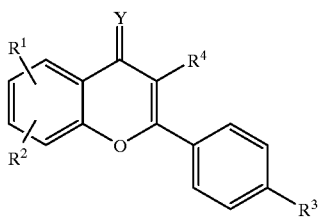

(I)

wherein

Y is an oxygen atom or a sulfur atom;

$R^1$ and $R^2$, identical to or different from each other, are independently a hydrogen atom, a halogen atom, a $C_1$–$C_6$ lower alkyl group, a trifluromethyl group, an alkoxy group, a hydroxy group, a nitro group, a nitrile group, or a carboxyl group;

$R^3$ is a group of a formula: $S(O)nR^5$ wherein n is an integer of 0~2, $R^5$ is a hydrogen atom, a $C_1$–$C_6$ lower alkyl group, or a group of a formula: $NR^6R^7$ wherein $R^6$ and $R^7$, identical to or different from each other, are independently a hydrogen atom, or a $C_1$–$C_6$ lower alkyl group;

$R^4$ is oxazolyl, benzo[b]thienyl, furanyl, thienyl, naphthyl, thiazolyl, indolyl, pyrolyl, benzofuranyl, pyrazolyl, pyrazolyl substituted with a $C_1$–$C_6$ lower alkyl group, indanyl, pyrazinyl, or a substituted group presented by the following structures:

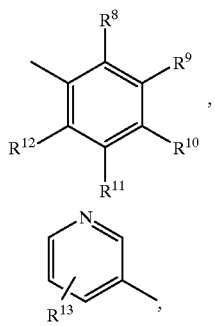

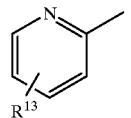

or

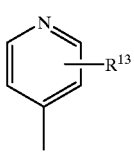

wherein $R^8$ through $R^{12}$, identical to or different from one another, are independently a hydrogen atom, a halogen atom, a $C_1$–$C_6$ lower alkyl group, a trifluromethyl group, an alkoxy group, a hydroxy group, a hydroxyalkyl group, a nitro group, a 3,4-methylenedioxy group, a group of a formula: $S(O)nR^5$, a group of a formula: $NR^6R^7$, a trifluromethoxy group, a nitrile group, a carboxyl group, an acetyl group, or a formyl group, wherein n, $R^5$, $R^6$ and $R^7$ have the same meaning as defined X and $R^3$ above; and $R^{13}$ is a hydrogen atom, a halogen atom, a $C_1$–$C_6$ lower alkyl group, a trifluromethyl group, a alkoxy group, a hydroxy group, a trifluromethoxy group, a carboxyl group, or an acetyl group.

Also, the diarylbenzopyran derivatives of the above-described general formula(I) could form pharmaceutically acceptable salts, which generally refer to the salts that could form alkaline-metal salts, acid-addition salts, or base-addition salts and are pharmaceutically acceptable because of their non-toxicity. The pharmaceutically acceptable acid-addition salts of the compound(I) are derived from the organic acid or inorganic acid. The inorganic acid used in the present invention, for example, is hydrochloric acid, bromic acid, iodic acid, nitric acid, carbonic acid, sulfuric acid or phosphoric acid. The organic acid used in the present invention, for example, is formic acid, acetic acid, propionic acid, succinic acid, aspartic acid, ascorbic acid, benzoic acid, benzenesulfonic acid, methylsulfonic acid, p-toluenesulfonic acid or salicylic acid.

The pharmaceutically acceptable base-addition salts of the compound(I) are metal salts derived from Al, Ca, Li, Mg, K, Na and Zn or organic salts derived from N, N'-dibenzylethylenediamine, choline, chloroprocaine, diethanolamine, ethylenediamine, N-methylglucamine and procaine.

Even though the use of diarylbenzopyran derivatives(I) of the present invention is not particulary limited, it is useful for treating, for example inflammatory diseases, or as analgesia for labor pain, headache or as antifebrile. The compound(I) of the present invention, not particularly limited, is also useful for treating arthritis such as rheumatic arthritis, spondylitis ankylopoietica, gouty arthritis, osteoarthritis. And the compound(I) of the present invention is useful for treating asthma, bronchitis, dysmenorrhea, tendinitis, bursitis and also useful for treating skin-related diseases such as psoriasis, eczema, bum and dermatitis. Also, the compound(I) of the present invention is useful for treating diseases such as peptic ulcer, gastritis, topical enteritis, colic diverticulitis, gastrointestinal bleeding, and the like. Also the compound(I) of the present invention coud be used in treating cancer by inhibiting the transformation of cell and the growth of metastatic cancer. Moreover, it could be used in treating and preventing diseases, which show abnormality in cyclooxygenase-involving proliferation such as diabetic retinopathy and cancerous vascularization. And it is effective in treating Alzheimer's disease and used in preventing osteoporosis and in treating glaucoma.

Also, the compound(I) of the present invention can be used as a substitute drug for conventional non-steroidal antiinflammatory drugs because it shows high activity and specificity on COX-2. Particulary, the compound of the present invention could be used as a substitute drug in treating patients who are suffering from hypoprothrombinemia, hemophilia or kidney disease, or waiting for surgery or has recurrent gastrointestinal tract disorders such as agglutination abnormality cause by anti-coagulant uptake.

In addition to that the compound of the present invention, as we described above, is useful for treating human diseases, it also could be used in treating warm-blooded animals such as mice, house mice, horses, lambs, dogs, cats and etc.

Also, the compound (I) of the present invention can be used for substituting all or parts of active ingredients in the existing non-steroidal inflammatory preparations. In other words, diarylbenzopyran derivatives or their pharmaceutically acceptable salts could be used alone or combined with one of or some of the following components:

(i) pain relievers containing acetoaminophen or phenacetin;
(ii) potentiators containing caffeine;
(iii) $H_2$-antagonists;
(iv) decongestants containing aluminum hydroxide, magnesium hydroxide, simethicone, phenylephrine, phenylpropanolamine, pseudophedrine, oxymetazoline, propylhexedrine or levodeoxyephedrine;
(v) antitussives containing codeine, hydrocodone, caramiphene, carbetapentane or dextramethorphan;
(vi) prostaglandins containing misoprostol, enprostil, riprostil, ornoprostol or rosaprostol;
(vii) diuretics;
(viii) antihistamines having or without having sedative action:

The preferred compound(I) of the present invention includes one of the following compounds:
2-(4-(Methylsulfonyl)phenyl)-3-phenyl-4H-1-benzopyran-4-one,
2-(4-(Methylsulfonyl)phenyl)-3-(4-(methylthio)phenyl)-4H-1-benzopyran-4-one,
3-(2-Methoxyphenyl)-2-(4-(methylsulfonyl)phenyl)-4H-1-benzopyran-4-one,
3-(4-Fluorophenyl)-2-(4-(methylsulfonyl)phenyl)-4H-1-benzopyran-4-one,
3-(2-Chlorophenyl)-2-(4-(methylsulfonyl)phenyl)-4H-1-benzopyran-4-one,
3-(4-(N,N-Dimethylamino)phenyl)-2-(4-(methylsulfonyl)phenyl)-4H-1-benzopyran-4-one,
3-(4-(N-Methylamino)phenyl)-2-(4-(methylsulfonyl)phenyl)-4H-1-benzopyran-4-one,
2-(4-(Methylsulfonyl)phenyl)-3-(4-trifluoromethoxyphenyl)-4H-1-benzopyran-4-one,
3-(3-Methoxyphenyl)-2-(4-(methylsulfonyl)phenyl)-4H-1-benzopyran-4-one,
3-(4-Isopropylphenyl)-2-(4-(methylsulfonyl)phenyl)-4H-1-benzopyran-4-one,
3-(4-Ethylphenyl)-2-(4-(methylsulfonyl)phenyl)-4H-1-benzopyran-4-one,
3-(4-Hydroxymethylphenyl)-2-(4-(methylsulfonyl)phenyl)-4H-1-benzopyran-4-one,
2-(4-(Methylsulfonyl)phenyl)-3-(4-trifluoromethylphenyl)-4H-1-benzopyran-4-one,
3-(4-Hydroxyphenyl)-2-(4-(methylsulfonyl)phenyl)-4H-1-benzopyran-4-one,
3-(2,3-Difluorophenyl)-2-(4-(methylsulfonyl)phenyl)-4H-1-benzopyran-4-one,
3-(3,5-Difluorophenyl)-2-(4-(methylsulfonyl)phenyl)-4H-1-benzopyran-4-one,
3-(2Hydroxyphenyl)-2-(4-(methylsulfonyl)phenyl)-4H-1-benzopyran-4-one,
3-(2,4-Difluorophenyl)-2-(4-(methylsulfonyl)phenyl)-4H-1-benzopyran-4-one,
3-(4-Methylphenyl)-2-(4-(methylsulfonyl)phenyl)-4H-1-benzopyran-4-one,
3-(2,4-Dichlorophenyl)-2-(4-(methylsulfonyl)phenyl)-4H-1-benzopyran-4-one,
3-(4-Acetylphenyl)-2-(4-(methylsulfonyl)phenyl)-4H-1-benzopyran-4-one,
3-(2,4-Dimethylphenyl)-2-(4-(methylsulfonyl)phenyl)-4H-1-benzopyran-4-one,
3-(4-Formylphenyl)-2-(4-(methylsulfonyl)phenyl)-4H-1-benzopyran-4-one,
3-(4-Carboxyphenyl)-2-(4-(methylsulfonyl)phenyl)-4H-1-benzopyran-4-one,
3-(4-Chloro-3-fluorophenyl)-2-(4-(methylsulfonyl)phenyl)-4H-1-benzopyran-4-one,
3-(4-Methoxyphenyl)-2-(4-(methylsulfonyl)phenyl)-4H-1-benzopyran-4-one,
3-(3,4-Dichlorophenyl)-2-(4-(methylsulfonyl)phenyl)-4H-1-benzopyran-4-one,
3-(2-Fluorophenyl)-2-(4-(methylsulfonyl)phenyl)-4H-1-benzopyran-4-one,
3-(4-Fluorophenyl)-5-methoxy-2-(4-(methylsulfonyl)phenyl)-4H-1-benzopyran-4-one,
3-(4-Fluorophenyl)-5-hydroxy-2-(4-(methylsulfonyl)phenyl)-4H-1-benzopyran-4-one,
3-(3,5-Dichlorophenyl)-2-(4-(methylsulfonyl)phenyl)-4H-1-benzopyran-4-one,
3-(N-methyl-3-pyrazolyl)-2-(4-(methylsulfonyl)phenyl)-4H-1-benzopyran-4-one,
3-(4-Chlorophenyl)-2-(4-(methylsulfonyl)phenyl)-4H-1-benzopyran-4-one,
6-Chloro-3-(4-fluorophenyl)-2-(4-(methylsulfonyl)phenyl)-4H-1-benzopyran-4-one,
2-(4-(methylsulfonyl)phenyl)-3-(3-nitrophenyl)-4H-1-benzopyran-4-one,
3-(3,4-Difluorophenyl)-2-(4-(methylsulfonyl)phenyl)-4H-1-benzopyran-4-one,
2-(4-(methylsulfonyl)phenyl)-3-(1-naphthyl)-4H-1-benzopyran-4-one,
3-(3-Methylphenyl)-2-(4-(methylsulfonyl)phenyl)-4H-1-benzopyran-4-one,
3-(2-Methylphenyl)-2-(4-(methylsulfonyl)phenyl)-4H-1-benzopyran-4-one,
3-(3-Chloro-4-fluorophenyl)-2-(4-(methylsulfonyl)phenyl)-4H-1-benzopyran-4-one,
3-(4-Bromophenyl)-2-(4-(methylsulfonyl)phenyl)-4H-1-benzopyran-4-one, 3-(2,3-Dichlorophenyl)-2-(4-(methylsulfonyl)phenyl)-4H-1-benzopyran-4-one,
3-(3-Fluorophenyl)-2-(4-(methylsulfonyl)phenyl)-4H-1-benzopyran-4-one,
3-(3-Chlorophenyl)-2-(4-(methylsulfonyl)phenyl)-4H-1-benzopyran-4-one,
2-(4-(Methylsulfonyl)phenyl)-3-(2-oxazolyl)-4H-1-benzopyran-4-one,
6-Fluoro-2-(4-fluorophenyl)-3-(4-(methylsulfonyl)phenyl)-4H-1-benzopyran-4-one,
3-(2-Benzo[b]thienyl)-2-(4-(methylsulfonyl)phenyl)-4H-1-benzopyran-4-one,
3-(2-Chloro-5-pyridinyl)-7-fluoro-2-(4-(methylsulfonyl)phenyl)-4H-1-benzopyran-4-one,
7-Fluoro-2-(4-(methylsulfonyl)phenyl)-3-(3-pyridinyl)-4H-1-benzopyran-4-one,
2-(4-(Methylsulfonyl)phenyl)-3-(2-pyridinyl)-4H-1-benzopyran-4-one,
2-(4-(Methylsulfonyl)phenyl)-3-(3-pyridinyl)-4H-1-benzopyran-4-one,
2-(4-(Methylsulfonyl)phenyl)-3-(4-pyridinyl)-4H-1-benzopyran-4-one,
6-Fluoro-2-(4-(methylsulfonyl)phenyl)-3-(3-pyridinyl)-4H-1-benzopyran-4-one,
7-Fluoro-3-(2-methoxy-5-pyridinyl)-2-(4-(methylsulfonyl)phenyl)-4H-1-benzopyran-4-one,
3-((3,4-methylenedioxy)phenyl)-2-(4-(methylsulfonyl)phenyl)-4H-1-benzopyran-4one,
2-(4-(Methylsulfonyl)phenyl)-3-(2-thiazolyl)-4H-1-benzopyran-4-one,
3-(Benzofuran-2-yl)-2-(4-(methylsulfonyl)phenyl)-4H-1-benzopyran-4-one,
2-(4-(Methylsulfonyl)phenyl)-3-(2-thienyl)-4H-1-benzopyran-4-one,
2-(4-(Methylsulfonyl)phenyl)-3-(2-pyrazinyl)-4H-1-benzopyran-4-one,
3-(2-Methyl-5-pyridinyl)-2-(4-(methylsulfonyl)phenyl)-4H-1-benzopyran-4-one,
3-(2-Methoxy-5-pyridinyl)-2-(4-(methylsulfonyl)phenyl)-4H-1-benzopyran-4-one,
6-Fluoro-3-(2-methyl-5-pyridinyl)-2-(4-(methylsulfonyl)phenyl)-4H-1-benzopyran-4-one,
6-Fluoro-3-(2-methoxy-5-pyridinyl)-2-(4-(methylsulfonyl)phenyl)-4H-1-benzopyran-4-one,
3-(2-Chloro-5-pyridinyl)-2-(4-(methylsulfonyl)phenyl)-4H-1-benzopyran-4-one,
3-(2-Chloro-5-pyridinyl)-6-fluoro-2-(4-(methylsulfonyl)phenyl)-4H-1-benzopyran-4-one,
3-(2-Fluoro-5-pyridinyl)-2-(4-(methylsulfonyl)phenyl)-4H-1-benzopyran-4-one,
6-fluoro-3-(2-fluoro-5-pyridinyl)-2-(4-(methylsulfonyl)phenyl)-4H-1-benzopyran-4-one,
7-fluoro-3-(2-fluoro-5-pyridinyl)-2-(4-(methylsulfonyl)phenyl)-4H-1-benzopyran-4-one,
3-(4-Chloro-3-pyridinyl)-2-(4-(methylsulfonyl)phenyl)-4H-1-benzopyran-4-one,
3-(4-Fluorophenyl)-6-methoxy-2-(4-(methylsulfonyl)phenyl)-4H-1-benzopyran-4-one,
2-(4-(Methylsulfonyl)phenyl)-3-(2-trifluoromethyl-5-pyridinyl)-4H-1-benzopyran-4-one,
3-(2-Fluoro-3-pyridinyl)-2-(4-(methylsulfonyl)phenyl)-4H-1-benzopyran-4-one,
3-(2-Chloro-3-pyridinyl)-2-(4-(methylsulfonyl)phenyl)-4H-1-benzopyran-4-one,
3-(5-Bromo-3-pyridinyl)-2-(4-(methylsulfonyl)phenyl)-4H-1-benzopyran-4-one,
3-(2-Furyl)-2-(4-(methylsulfonyl)phenyl)-4H-1-benzopyran-4-one,
3-(5-Indanyl)-2-(4-(methylsulfonyl)phenyl)-4H-1-benzopyran-4-one,
3-(4-Fluorophenyl)-6-methyl-2-(4-(methylsulfonyl)phenyl)-4H-1-benzopyran-4-one,
3-(4-Fluorophenyl)-6-hydroxy-2-(4-(methylsulfonyl)phenyl)-4H-1-benzopyran-4-one,
2-(4-(Aminosulfonyl)phenyl)-3-(2-methylphenyl)-4H-1-benzopyran-4-one,
2-(4-(Aminosulfonyl)phenyl)-3-phenyl-4H-1-benzopyran-4-one,
2-(4-(Aminosulfonyl)phenyl)-3-(3,4-difluorophenyl)-4H-1-benzopyran-4-one,
2-(4-(Aminosulfonyl)phenyl)-3-(4-chloro-3-fluorophenyl)-4H-1 benzopyran-4-one,
2-(4-(Aminosulfonyl)phenyl)-3-(3-chloro-4-fluorophenyl)-4H-1-benzopyran-4-one,
2-(4-(Aminosulfonyl)phenyl)-3-(3,4-dichlorophenyl)-4H-1-benzopyran-4-one,
2-(4-(Aminosulfonyl)phenyl)-3-(2-chlorophenyl)-4H-1-benzopyran-4-one,
2-(4-(Aminosulfonyl)phenyl)-3-(3-chlorophenyl)-4H-1-benzopyran-4-one,
2-(4-(Aminosulfonyl)phenyl)-3-(4-chlorophenyl)-4H-1-benzopyran-4-one,
2-(4-(Aminosulfonyl)phenyl)-3-((4-methylthio)phenyl)-4H-1-benzopyran-4-one,
2-(4-(Aminosulfonyl)phenyl)-3-((3,4-methylenedioxy)phenyl)-4H-1-benzopyran-4-one,
2-(4-(Aminosulfonyl)phenyl)-3-(2,3-difluorophenyl)-4H-1-benzopyran-4-one,
2-(4-(Aminosulfonyl)phenyl)-3-(3-fluorophenyl)-4H-1-benzopyran-4-one,
2-(4-(Aminosulfonyl)phenyl)-3-(2-fluorophenyl)-4H-1-benzopyran-4-one,
2-(4-(Aminosulfonyl)phenyl)-3-(2,4-difluorophenyl)-4H-1-benzopyran-4-one,
2-(4-(Aminosulfonyl)phenyl)-3-(3-methylphenyl)-4H-1-benzopyran-4-one,
2-(4-(Aminosulfonyl)phenyl)-3-(2-methoxyphenyl)-4H-1-benzopyran-4-one,
2-(4-(Aminosulfonyl)phenyl)-6-fluoro-3-(2-fluoro-5-pyridinyl)-4H-1-benzopyran-4-one,
2-(4-(Aminosulfonyl)phenyl)-3-(4-methylphenyl)-4H-1-benzopyran-4-one,
2-(4-(Aminosulfonyl)phenyl)-3-(4-methoxyphenyl)-4H-1-benzopyran-4-one,
2-(4-(Aminosulfonyl)phenyl)-7-fluoro-3-(2-methoxy-5-pyridinyl)-4H-1-benzopyran-4-one,
2-(4-(Aminosulfonyl)phenyl)-3-(3-methoxyphenyl)-4H-1-benzopyran-4-one,
2-(4-(Aminosulfonyl)phenyl)-3-(4-fluorophenyl)-4H-1-benzopyran-4-one,
2-(4-(Aminosulfonyl)phenyl)-3-(2-chloro-5-pyridinyl)-7-fluoro-4H-1-benzopyran-4-one,
2-(4-(Aminosulfonyl)phenyl)-3-(3,5-difluorophenyl)-4H-1-benzopyran-4-one,
2-(4-(Aminosulfonyl)phenyl)-3-(2-pyridinyl)-4H-1-benzopyran-4-one,
2-(4-(Aminosulfonyl)phenyl)-3-(3-pyridinyl)-4H-1-benzopyran-4-one,
2-(4-(Aminosulfonyl)phenyl)-6-fluoro-3-(3-pyridinyl)-4H-1-benzopyran-4-one,
2-(4-(Aminosulfonyl)phenyl)-7-fluoro-3-(3-pyridinyl)-4H-1-benzopyran-4-one,
2-(4-(Aminosulfonyl)phenyl)-3-(2-chloro-5-pyridinyl)-4H-1-benzopyran-4-one,
2-(4-(Aminosulfonyl)phenyl)-3-(2-chloro-5-pyridinyl)-6-fluoro-4H-1-benzopyran-4-one, 2-(4-(Aminosulfonyl)phenyl)-3-(2-fluoro-5-pyridinyl)-4H-1-benzopyran-4-one,
2-(4-(Aminosulfonyl)phenyl)-7-fluoro-3-(2-fluoro-5-pyridinyl)-4H-1-benzopyran-4-one,
2-(4-(Aminosulfonyl)phenyl)-3-(2-methyl-5-pyridinyl)-4H-1-benzopyran-4-one,
2-(4-(Aminosulfonyl)phenyl)-3-(2-methoxy-5-pyridinyl)-4H-1-benzopyran-4-one,
2-(4-(Aminosulfonyl)phenyl)-6-fluoro-3-(2-methoxy-5-pyridinyl)-4H-1-benzopyran-4-one,
2-(4-(Arninosulfonyl)phenyl)-3-(4-pyridinyl)-4H-1-benzopyran-4-one,
2-(4-(Aminosulfonyl)phenyl)-3-(2-thienyl)-4H-1-benzopyran-4-one,
2-(4-(Aminosulfonyl)phenyl)-3-(2-furyl)-4H-1-benzopyran-4-one,
2-(4-(Aminosulfonyl)phenyl)-6-fluoro-3-(4-fluorophenyl)-4H-1-benzopyran-4-one,
2-(4-(Aminosulfonyl)phenyl)-6-fluoro-3-phenyl-4H-1-benzopyran-4-one,
2-(4-(Aminosulfonyl)phenyl)-6-fluoro-3-(4-methylphenyl)-4H-1-benzopyran-4-one,
2-(4-(Aminosulfonyl)phenyl)-6-fluoro-3-(4-chlorophenyl)-4H-1-benzopyran-4-one,
2-(4-(Aminosulfonyl)phenyl)-6-fluoro-3-(3-fluorophenyl)-4H-1-benzopyran-4-one,
2-(4-(Aminosulfonyl)phenyl)-7-fluoro-3-(4-fluorophenyl)-4H-1-benzopyran-4-one,
2-(4-(Aminosulfonyl)phenyl)-7-fluoro-3-(3-fluorophenyl)-4H-1-benzopyran-4-one,
2-(4-(Aminosulfonyl)phenyl)-7-fluoro-3-(2-fluorophenyl)-4H-1-benzopyran-4-one,
2-(4-(Aminosulfonyl)phenyl)-7-fluoro-3-(3,4-dichlorophenyl)-4H-1-benzopyran-4-one,
2-(4-(Aminosulfonyl)phenyl)-8-chloro-3-(4-fluorophenyl)-5-hydroxy-4H-1-benzopyran-4-one,
2-(4-(Aminosulfonyl)phenyl)-8-chloro-3-(4-fluorophenyl)-5-methoxy-4H-1-benzopyran-4-one,
2-(4-(Aminosulfonyl)phenyl)-6-methoxy-3-(4-fluorophenyl)-4H-1-benzopyran-4-one,
2-(4-(Aminosulfonyl)phenyl)-7-methoxy-3-(4-fluorophenyl)-4H-1-benzopyran-4-one,
2-(4-(Aminosulfonyl)phenyl)-6-hydroxy-3-(4-fluorophenyl)-4H-1-benzopyran-4-one,
2-(4-(Methylsulfonyl)phenyl)-3-phenyl-4H-1-benzopyran-4-thione,
3-(4-Fluorophenyl)-2-(4-(methylsulfonyl)phenyl)-4H-1-benzopyran-4-thione,
6-Fluoro-3-(4-fluorophenyl)-2-(4-(methylsulfonyl)phenyl)-4H-1-benzopyran-4-thione,
3-(2-Fluorophenyl)-2-(4-(methylsulfonyl)phenyl)-4H-1-benzopyran-4-thione,
7-Fluoro-2-(4-(methylsulfonyl)phenyl)-3-(3-pyridinyl)-4H-1-benzopyran-4-thione,
3-(3-Fluorophenyl)-2-(4-(methylsulfonyl)phenyl)-4H-1-benzopyran-4-thione,
3-(2-Methylphenyl)-2-(4-(methylsulfonyl)phenyl)-4H-1-benzopyran-4-thione,
3-(4-Methylphenyl)-2-(4-(methylsulfonyl)phenyl)-4H-1-benzopyran-4-thione,
3-(3-Methylphenyl)-2-(4-(methylsulfonyl)phenyl)-4H-1-benzopyran-4-thione,
3-(4-Methoxyphenyl)-2-(4-(methylsulfonyl)phenyl)-4H-1-benzopyran-4-thione,
6-Fuoro-2-(4-(methylsulfonyl)phenyl)-3-(3-pyridinyl)-4H-1-benzopyran-4-thione,
3-(2-Chlorophenyl)-2-(4-(methylsulfonyl)phenyl)-4H-1-benzopyran-4-thione,
3-(2,3-Dichlorophenyl)-2-(4-(methylsulfonyl)phenyl)-4H-1-benzopyran-4-thione,
3-(3,4-Dichlorophenyl)-2-(4-(methylsulfonyl)phenyl)-4H-1-benzopyran-4-thione,
3-(3-Chlorophenyl)-2-(4-(methylsulfonyl)phenyl)-4H-1-benzopyran-4-thione,
3-(4-Chlorophenyl)-2-(4-(methylsulfonyl)phenyl)-4H-1-benzopyran-4-thione,
3-(3-Methoxyphenyl)-2-(4-(methylsulfonyl)phenyl)-4H-1-benzopyran-4-thione,
2-(4-(Methylsulfonyl)phenyl)-3-(4-trifluoromethylphenyl)-4H-1-benzopyran-4-thione,
3-(3-Chloro-4-fluorophenyl)-2-(4-(methylsulfonyl)phenyl)-4H-1-benzopyran-4-thione,
2-(4-(Methylsulfonyl)phenyl)-3-(3-pyridinyl)-4H-1-benzopyran-4-thione,
2-(4-(Aminosulfonyl)phenyl)-6-fluoro-3-(3-pyridinyl)-4H-1-benzopyran-4-thione,
2-(4-(Aminosulfonyl)phenyl)-3-(3-pyridinyl)-4H-1-benzopyran-4-thione,
2-(4-(Aminosulfonyl)phenyl)-3-(4-fluorophenyl)-4H-1-benzopyran-4-thione,
2-(4-(Aminosulfonyl)phenyl)-3-(2-fluorophenyl)-4H-1-benzopyran-4-thione,
2-(4-(Aminosulfonyl)phenyl)-3-(4-chlorophenyl)-4H-1-benzopyran-4-thione,
2-(4-(Aminosulfonyl)phenyl)-3-phenyl-4H-1-benzopyran-4-thione,
2-(4-(Aminosulfonyl)phenyl)-6-fluoro-3-(4-fluorophenyl)-4H-1-benzopyran-4-thione,
2-(4-(Aminosulfonyl)phenyl)-7-fluoro-3-(3-pyridinyl)-4H-1-benzopyran-4-thione The diarylbenzop,ran derivatives of the present invention can be prepared by reaction schemes 1 through 6. Wherein $R^1$, $R^2$, $R^3$ and $R^4$ in the reaction schems have the same meanings as defined above.

[Reaction Scheme 1]

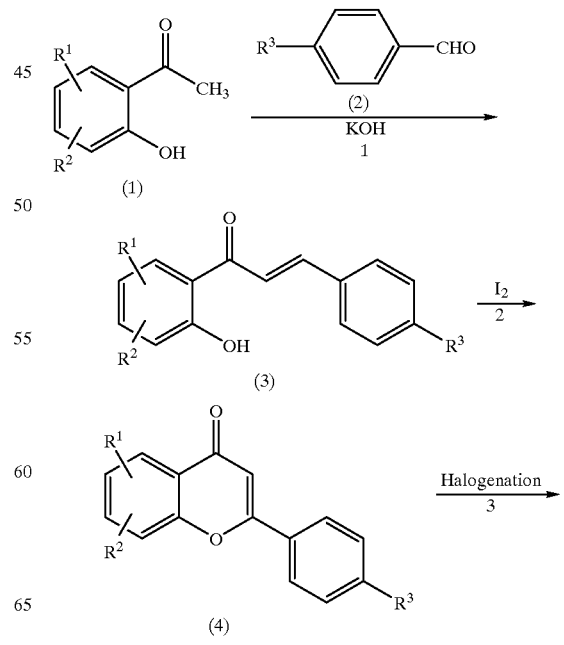

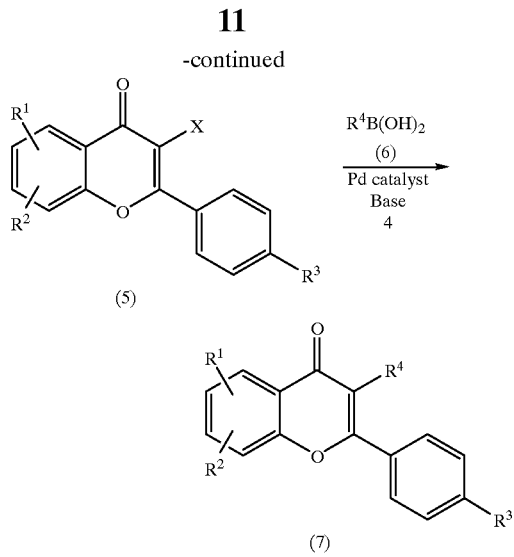

It represents a four-step reaction of preparing diarylbenzopyran derivative. In Step 1, chalcone(3) is prepared by condensation of substituted acetophenon(1) and substituted aldehyde(2) in the presence of KOH base. In Step 2, flavone derivative is prepared by cyclization of calcone(3) by adding $I_2$ as a catalyst. A suitable solvent of this step is dimethyl sulfoxide(DMSO). In Step 3, 3-halogenized flavone derivative is prepared by reaction of flavone derivative(4) either with $I_2$ or N-bromosuccinimide(NBS). In Step 4, benzopyran derivative(7) in which $R^4$ group at position 3 is substituted is prepared by cross-coupling reaction of substituted flavone derivative(5) with $R^4$ group substituted boronic acid using Paladium as a catalyst[(Synth. Commun., 11, 513 (1981)].

[Reaction Scheme 2]

It represents a 3-step transformed reaction of preparing diarylbenzopyran derivative. In Step 1, compound(8) is prepared by the reaction of flavone derivative(4) having methylthio group as $R^3$ with $I_2$ in the presence of Lithium diisopropylamide(LDA) base, at a temperature of –78° C. [J. Chem. Soc. Perkin Trans. I. 799(1985)]. In Step 2, methylsulfonylflavone(10) is prepared by oxidation with oxone(potassium peroxymonosulfate) or 3-chloroperoxybenzoic acid(MCPBA). In Step 3, benzopyran derivative(11) is prepared by cross-coupling reaction of compound(10) with boronic acid(6) using paladium as catalyst.

Alternatively, compound(11) could be prepared by the following method: First, methylsulfonyl group substituted flavone derivative(9) is prepared by oxidizing compound(4) having methylthio group as $R^3$ with oxone; and then compound(10) is prepared by reacting compound(9) with $I_2$ and [Bis(trifluoroacetoxy)iodo]benzene(BTI); and benzopyran derivative(11) is prepared by Step 3 of the above reaction.

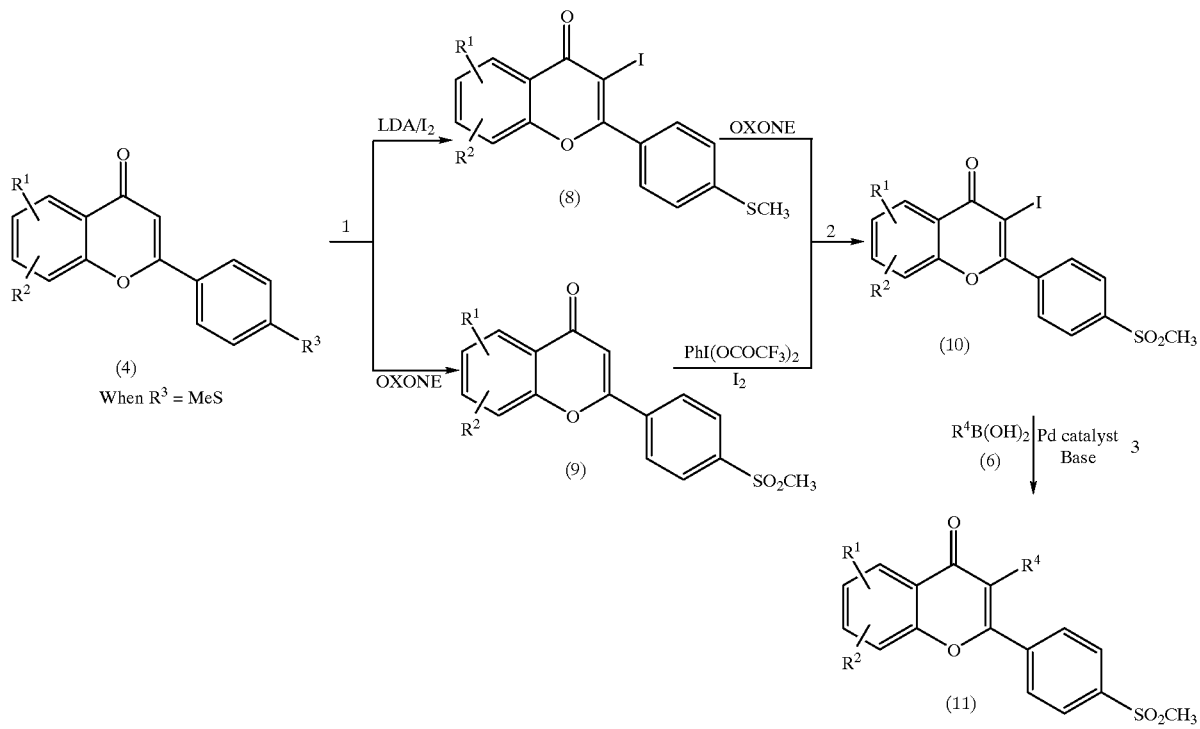

[Reaction Scheme 3]

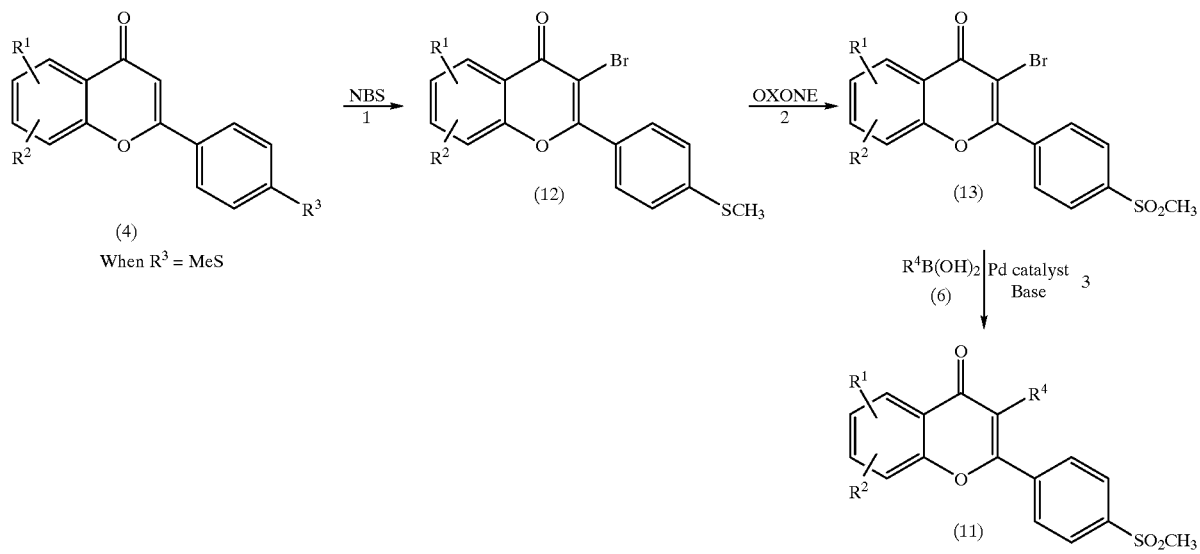

It represents the 3-step modified reaction of preparing diarylbenzopyran derivative. In Step 1, bromoflavone(12) is prepared by refluxing flavone derivative(4) having methylthio group as $R^3$ in chloroform in the presence of N-bromosuccinimide(NBS). In Step 2, methylsulfonylflavone(13) is prepared by oxidation with oxone or MCPBA. In Step 3, benzopyran derivative(11) is substituted is prepared by cross-coupling reaction of compound(13) with boronic acid(6) using paladium catalyst.

[Reaction Scheme 4]

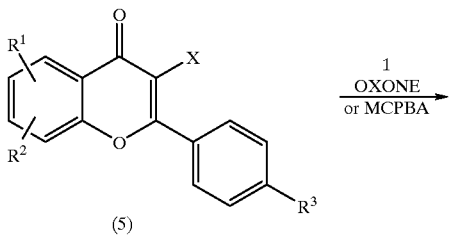

It represents the 1-step reaction of preparing diarylbenzopyranthione derivative. Benzopyranthione derivative(14) is prepared by refluxing diarylbenzopyran derivative with Lawesson reagent(2,4-bis(4-methoxyphenyl)-1,3-dithia-2,4-diphosphentan-2,4-disulfate; Org. Synth. Coll., 7, 372 (1990)) or $P_4S_{10}$ in toluenet.

[Reaction Scheme 5]

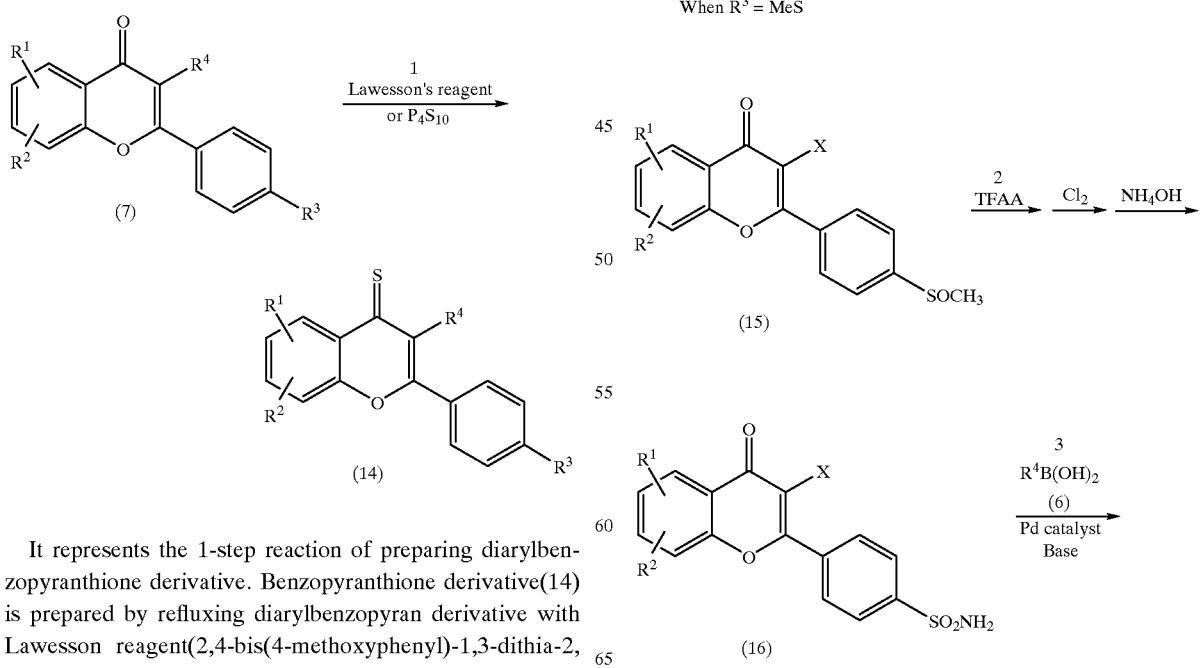

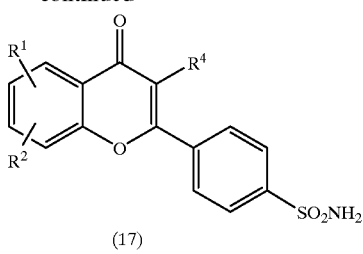

It represents the 3-step reaction of preparing diarylbenzopyran derivative. In Step 1, methylsulfinylflavone derivative(15) is prepared by oxidizing compound(5) with oxone or MCPBA. In Step 2, aminosulfonylflavone derivative is prepared by reacting flavone derivative(15) with trifluoroacetic anhydride(TFAA), chlorine gas, ammonium hydroxide. In Step 3, benzopyran derivative(17) is prepared by cross-coupling reaction of aminosulfonylflavone deriative(16) with boronic acid(6) using paladium catalyst.

[Reaction Scheme 6]

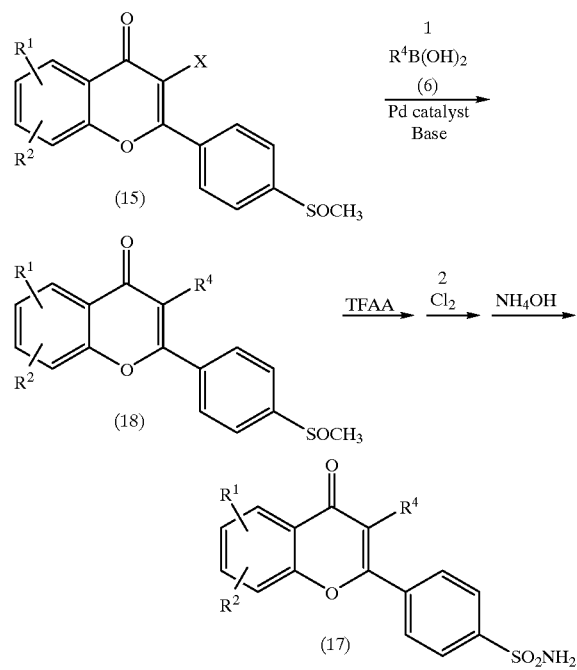

It represents the modified reaction of preparing diarylbenzopyran derivative. In Step 1, benzopyran derivative(18) is prepared by cross-coupling reaction of flavone derivative (15) prepared in reaction scheme 5, Step 1 with boronic acid(6) using paladium catalyst. In next step, benzopyran derivatives(17) is prepared by having the same condition of the reaction scheme 5, Step 2.

The present invention will be described in more detail by the following examples and experimental examples, but it must not be construed that this invention is confined by them.

EXAMPLE 1

3-(4-Fluorophenyl)-2-(4-(methylsulfonyl)phenyl)-4H-1-benzo-pyran-4-one

Step 1; 2'-Hydroxy-4-(methylthio)chalcone

To a solution of 2'-hydroxyacetophenone(10.88 g, 80 mmol) and 4-(methylthio)benzaldehyde(12.16 g, 80 mmol) in ethanol(120 ml) at a temperature of 0° C. was added a solution of KOH (8.96 g, 2.0 equivalent) in water(40 ml) dropwise. The mixture was stirred at room temperature for 24 hours. The solution was acidified with 3N HCl(88 ml) and extracted two times with $CH_2Cl_2$ (100 ml per each). The organic layer was washed with saturated NaCl and dried over anhydrous $MgSO_4$ and filtered and concentrated under reduced pressure. The recrystallization of the residue with $CH_2Cl_2$ and petroleum ether yielded the title compound as a yellow solid (42.01 g, 65%).

mp: 98~100° C.

$^1$H NMR(CDCl$_3$, 300 MHz): δ7.94~7.86(2H, m), 7.65~7.47(6H, m), 7.29~7.25(2H, m), 7.05~6.92(2H, m), 2.53(3H, s)

IR(KBr): 2911, 1658, 1433, 1306, 1090, 1013 cm$^{-1}$

Step 2; 2-(4-(Methlthio)phenyl)-4H-1-benzopyran-4-one

2'-hydroxy-4-(methylthio)chalcone(9.5 g, 35.15 mmol) from Step 1 and catalytic amount of $I_2$ was dissolved in dimethylsulfoxide(;DMSO, 100 ml) and the resulting mixture was stirred at a temperature of 180° C. for half an hour. After identifying the reaction being complete by TLC, the resulting dark solution was poured into excessive ice-water (about 300 ml) and stirred for 10 minutes. The mixture was extracted two times with $CH_2Cl_2$ (100 ml per each). And the organic layer was washed with saturated $Na_2S_2O_3$(100 ml), brine and dried over anhydrous $MgSO_4$ and filtered and concentrated under reduced pressure. The recrystallization of the residue with $CH_2Cl_2$ and petroleum ether yielded the title compound as a light yellow solid(7.54 g, 80%).

mp: 110~112° C.

$^1$H NMR(CDCl$_3$, 300 MHz): δ8.25~8.22(m, 1H), 7.86~7.83(m, 2H), 7.73~7.66(1H, m), 7.58~7.55(m, 1H), 7.45~7.40(1H, m), 7.37~7.33(2H, m), 6.83(1H, s), 2.55(3H, s)

IR(KBr): 1654, 1594, 1464, 1379, 1099 cm$^{-1}$

Step 3; 3-Iodo-2-(4-(methylthio)phenyl)-4H-1-benzopyran-4-one

To a solution of 2-(4-(methylthio)phenyl)-4H-1-benzopyran-4-one(0.20 g, 0.75 mmol) from Step 2 in anhydrous tetrahydrofluran(THF, 15 ml) was added 2M LDA (0.38 ml, 1 equivalent) by syringe with stirring at a temperature of -78° C. for 15 minutes under Argon gas atmosphere and then iodine(0.19 g, 0.75 mmol) in THF(5 ml) was added. The mixture was warmed to room temperature and then stirred for 12 hours. After the reaction being complete, the reaction mixture was poured into saturated $Na_2S_2O_3$(100 ml) and stirred for 1 hour, and the mixture was extracted two times with $CH_2Cl_2$ (30 ml per each) and the organic layer was washed with brine and dried over anhydrous $MgSO_4$ and filtered. The residue was subjected to flash chromatography using a mixture of hexane:ethyl acetate(7:1) as an eluant to afford the title compound as a pale yellow solid (0.23 g, 78%).

mp: 150~152° C.

$^1$H NMR(CDCl$_3$, 300 MHz): δ8.30~8.27(1H, m), 7.77~7.74(2H, m), 7.73~7.70(1H, m), 7.51~7.44(2H, m), 7.38~7.35(2H, m), 2.57(3H, s)

IR(KBr): 3032, 2912, 1646, 1599, 1490, 1330, 1060, 752 cm$^{-1}$

Step 4; 3-Iodo-2-(4-(methylsulfonyl)phenyl)-4H-1-benzopyran-4-one

To a solution of 3-iodo-2-(4-(methylthio)phenyl)-4H-1-benzopyran-4-one(0.34 g, 0.86 mmol) from Step 3 in MeOH (10 ml) and THF(10 ml) was added a solution of Oxone (1.59 g, 2.59 mmol) in $H_2O$(10 ml) dropwise at a temperature of 0° C. The resulting mixture was stirred for 3 hours. And the solution was extracted two times with $CH_2Cl_2$ (20 ml per each), and the organic layer was washed with brine and dried over anhydrous $MgSO_4$. And the resulting solution was filtered and concentrated under reduced pressure. Recrystallization of the resulting residue with $CH_2Cl_2$ and petroleum ether yielded the title compound as a white solid(0.33 g, 90%)

mp: 164~165° C.

$^1$H NMR(CDCl$_3$, 300 MHz): δ8.33~8.29(1H, m), 8.15~8.12(2H, m), 8.03~7.99(2H, m), 7.80~7.74(1H, m), 7.53~7.49(2H, m), 3.16(3H, s)

IR(KBr): 1643, 1470, 1301, 1151, 960, 750 cm$^{-1}$

Step 5; 3-(4-Fluorophenyl)-2-(4-methylsulfonyl)phenyl)-4H-1-benzopyran-4-one

To a solution of 3-iodo-2-(4-(methylsulfonyl)phenyl)-4H-1-benzopyran-4-one (0.33 g, 90%) from Step 4, 4-fluorobenzeneboronic acid(0.036 g, 0.26 mmol) in toluene(1 ml) and EtOH(1 ml) was added 2M aqueous sodium carbonate (0.61 ml) and then tetrakis(triphenylphosphine)palladium(0.014 g, 0.012 mmol) and was stirred at a temperature of 90° C. for 4 hours. After being concentrated under reduced pressure, it was dissolved in dichloromethane(10 ml) and washed with water, brine. The organic layer was dried over anhydrous $MgSO_4$. And the resulting solution was filtered and concentrated under reduced pressure. The residue was subjected to flash chromatography using a mixture of hexane:ethyl acetate(1:1) as an eluant to yield the title compound as a pale yellow solid(0.046 g, 59%).

mp: 208~210° C.

$^1$H NMR(CDCl$_3$, 300 MHz): δ8.32~8.30(1H, m), 7.90~7.87(2H, d), 7.79~7.73(1H, m), 7.62~7.60(2H, d), 7.57~7.54(1H, d), 7.51~7.46(1H, m), 7.21~7.16(2H, m), 7.07~7.01(2H, m), 3.07(3H, s)

IR(KBr): 3017, 2922, 1640, 1509, 1468, 1378, 1290, 1230, 1155, 1142, 770 cm$^{-1}$

EXAMPLE 2–21

The inventive compounds of Examples 2–21 were produced by the same procedure described in Example 1, but substituting appropriate boronic acid or boronate for 4-fluorobenzeneboronic acid in Example 1, step 5. These compounds and their physical properties are shown in Table 1.

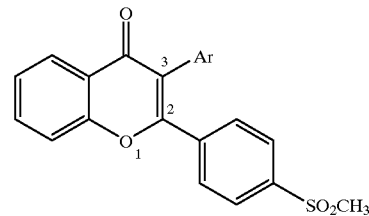

TABLE 1

| Example | 3-Ar | mp (° C.) | $^1$H NMR(CDCl$_3$, 300 MHz); δ | IR(KBr); cm$^{-1}$ |
|---|---|---|---|---|
| 2 | phenyl | 208–209 | 8.34~8.31(1H, m), 7.88~7.85(2H, m), 7.79~7.74(1H, m), 7.64~7.55(3H, m), 7.51~7.46(1H, m), 7.36~7.33(3H, m), 7.23~7.29(2H, m), 3.06(3H, s) | 3020, 2923, 1621, 1467, 1378, 1295, 1152 |
| 3 | 4-methyl-phenyl | 225 | 8.32~8.29(1H, m), 7.88~7.85(2H, d), 7.77~7.71(1H, m), 7.64~7.62(2H, d), 7.56~7.44(2H, m), 7.16~7.07(4H, m), 3.06(3H, s), 2.36(3H, s) | 1644, 1377, 1297 |
| 4 | 3-nitro-phenyl | 223–224 | 8.33~8.30(1H, m), 8.22~8.18.(1H, m), 8.10(1H, m), 7.93~7.90(2H, m), 7.83~7.77(1H, m), 7.63~7.49(6H, m), 3.06(3H, s), | 3089, 2914, 1640, 1526, 1462, 1350, 1143 |
| 5 | 2,4-dichloro-phenyl | 172–175 | 8.32~8.29(1H, m), 7.93~7.91(2H, m), 7.81~7.75(1H, m), 7.66~7.63(2H, m), 7.59~7.47(3H, m), 7.11~7.09(1H, d), 307(3H, s) | 1642, 1472, 1302, 1145, 774 |
| 7 | 2-thienyl | 165–167 | 8.33~8.30(1H, m), 8.15~8.12(2H, m), 8.02~7.99(2H, m), 7.95~7.93(1H, m), 7.80~7.72(2H, m), 7.55~7.46(3H, m), 3.16(3H, s) | 1668, 1300, 1157 |
| 8 | 4-acetyl-phenyl | 223–224 | 8.33~8.30(1H, m), 7.95~7.86(4H, m), 7.81~7.75(1H, m), 7.63~7.59(2H, m), 7.56(1H, s), 7.53~7.47(1H, m), 7.32(2H, m), 3.07(3H, s), 2.62(3H, s) | 1690, 1646, 1376, 1142 |
| 9 | 4-formyl-phenyl | 189–190 | 10.03(1H, s), 8.33~8.29(1H, m), 7.90~7.84(4H, m), 7.80~7.75(1H, m), 7.63~7.60(2H, m), 7.57(1H, s), 7.53~7.48(2H, m), 7.43~7.39(2H, m), 3.07(3H, s) | 2925, 1642, 1466, 1379, 1301, 1143 |
| 10 | 4-methoxy-phenyl | 212–213 | 8.32~8.29(1H, m), 7.89~7.86(2H, d), 7.77~7.71(1H, m), 7.65~7.62(2H, d), 7.56~7.53(1H, d), 7.47(1H, t), 7.14~7.11(2H, d), 6.89~6.86(2H, d), 3.82(3H, s), 3.06(3H, s) | 3006, 2915, 1632. 1608, 1513, 1465, 1376, 1300, 1141 |

TABLE 1-continued

| Example | 3-Ar | mp (° C.) | $^1$H NMR(CDCl$_3$, 300 MHz); δ | IR(KBr); cm$^{-1}$ |
|---|---|---|---|---|
| 11 | 3,4-dichloro-phenyl | 164–165 | 8.31~8.28(1H, m), 7.95~7.92(2H, m), 7.80~7.74(1H, m), 7.65~7.62(2H, m), 7.58~7.50(2H, m), 7.41~7.37(2H, m), 7.03~7.00(1H, m), 3.08(3H, s) | 1643, 1619, 1470, 1301, 1151 |
| 12 | 2-fluoro-phenyl | 180–181 | 8.33~8.30(1H, m), 7.90~7.87(2H, m), 7.79~7.74(1H, m), 7.66~7.63(2H, m), 7.58~7.46(2H, m), 7.40~7.32(1H, m), 7.24~7.20(3H, m), 3.06(3H, s) | 3089, 2931, 1640, 1469, 1376, 1300, 1142, 769 |
| 13 | 1-naphthyl | 193–194 | 8.34~8.30(1H, m), 7.91~7.77(3H, m), 7.74~7.61(4H, m), 7.54~7.43 (5H, m), 7.44~7.36(1H, m), 7.20~7.17(1H, m), 2.96(3H, s) | 2925, 1638, 1464, 1317, 1156, 764 |
| 14 | 2,3-dichloro-phenyl | 435–137 | 8.32~8.29(1H, m), 7.93~7.91(2H, m), 7.81~7.75(1H, m), 7.66~7.63(2H, m), 7.59~7.47(3H, m), 7.11~7.09(1H, d), 3.07(3H, s) | 1642, 1607, 1468, 1381, 1309, 1145, 772 |
| 15 | 3-pyridinyl | 220–221 | 8.57~8.54(1H, m), 8.33~8.29(2H, m), 7.92~7.88(2H, m), 7.82~7.70(2H, m), 7.62~7.48(4H, m), 7.37~7.34(1H, m), 3.07(3H, s) | 3052, 2923, 1639, 1466, 1381, 1301, 1156, 787 |
| 16 | 4-pyridinyl | 204–205 | 8.61~8.58(2H, m), 8.33~8.29(1H, m), 7.93~7.89(2H, m), 7.82~7.75(1H, m), 7.64~7.48(4H, m), 7.18~7.15(2H, m), 3.07(3H, s) | 2990, 1642, 1467, 1382, 1302, 1145, 784 |
| 17 | N-methyl-3-pyrazolyl | 202–203 | 8.31~8.28(1H, m), 8.01~7.98(2H, m), 7.83~7.79(3H, m), 7.75~7.69(1H, m), 7.52~7.43(2H, m), 6.97~6.96(1H, m), 3.91(3H, s), 3.07(3H, s) | 3091, 2925, 1641, 1467, 1313, 1154, 766 |
| 18 | 2-methoxy-5-pyridinyl | 226–227 | 8.31~8.28(1H, m), 7.93~7.86(3H, m), 7.79~7.73(1H, m), 7.66~7.63(2H, m), 7.60~7.45(3H, m), 6.80~6.77(1H, m), 3.92(3H, s), 3.09(3H, s) | 3654, 2924, 1641, 1601, 1496, 1466, 1369, 1301, 1144, 769 |
| 19 | 5-bromo-3-pyridinyl | 197–199 | 8.62~8.60(1H, m), 8.31~8.28(1H, m), 8.18~8.16(1H, m), 7.96~7.93(2H, m), 7.83~7.76(1H, m), 7.64~7.49(5H, m), 3.09(3H, s) | 3065, 2925, 1613, 1466, 1378, 1315, 1153, 765 |
| 20 | 2-methyl-5-pyridinyl | 195–196 | 8.31~8.28(1H, m), 8.21~8.19(1H, m), 7.92~7.88(2H, m), 7.79~7.73(1H, m), 7.63~7.46(5H, m), 7.21~7.18(1H, m), 3.08(3H, s), 2.57(3H, s) | 2924, 1641, 1466, 1400, 1301, 1144, 764 |
| 21 | 2-trifluoro-methyl-5-pyridinyl | 215–217 | 8.44~8.43(1H, m), 8.33~8.29(1H, m), 7.96~7.92(2H, m), 7.84~7.72(2H, m), 7.63~7.50(5H, m), 3.10(3H, s) | 3050, 1645, 1467, 1337, 1145, 1088, 761 |

EXAMPLE 22

3-(3-Methylphenyl)-2-(4-(methylsulfonyl)phenyl)-4H-1-benzopyran-4-one

Step 1; 3-Bromo-2-(4-(methylthio)phenyl)-4H-1-benzopyran-4-one

A solution of (4-(methylthio)phenyl)-4H-1-benzopyran-4-one(0.50 g, 1.86 mmol) and NBS(0.36 g, 2.05 mmol) in CHCl$_3$(30 ml) was heat to reflux for 5 hours. The resulting mixture was washed with saturated NaHCO$_3$, brine and dried over anhydrous MgSO$_4$, and filtered, and concentrated under reduced pressure. The residue was subjected to flash chromatography using a mixture of hexane: ethyl acetate (4:1) as an eluant to yield the title compound as a pale yellow solid(0.60 g, 93%).

mp: 162~163° C.

$^1$H NMR(CDCl$_3$, 300 MHz): δ8.30~8.27(1H, m), 7.84~7.80(2H, m), 7.74~7.69(1H, m), 7.51~7.43(2H, m), 7.38~7.34(2H, m), 2.55(3H, s)

IR(KBr): 1658, 1611, 1463, 1331, 1065, 753 cm$^{-1}$

Step 2; 3-Bromo-2-(4-(methylsulfonyl)phenyl)-4H-1-benzopyran-4-one

Following the same oxidation procedure of Example 1, Step 4, but replacing 3-iodo-2-(4-(methylthio)phenyl)-4H-1-benzopyran-4-one by 3-bromo-2-(4-(methylthio)-phenyl)-4H-1-benzopyran-4-one(0.6 g, 0.86 mmol) from Step 1, the 4H-1-benzopyran-4-one(0.6 g, 0.86 mmol) from Step 1, the title compound was obtained as a solid(0.59 g, 90%).

mp: 211~213° C.

$^1$H NMR(CDCl$_3$, 300 MHz): δ8.34~8.30(1H, m), 8.15~8.05(4H, m), 7.80~7.74(1H, m), 7.54~7.49(2H, m), 3.15(3H, s)

IR(KBr): 1646, 1310, 1146, 1075 cm$^{-1}$

Step 3; 3-(3-Methylphenyl)-2-(4-(methylsulfonyl)phenyl)-4H-1-benzopyran-4-one

Following the procedure of Example 1, Step 5, but substituting 3-bromo-2-(4-(methylsulfonyl)phenyl)-4H-1-benzopyran-4-one(0.18 g,0.47 mmol) for 3-iodo 2-(4-(methylsulfonyl)phenyl)-4H-1-benzopyran-4-one and m-tolylboronic acid(0.071 g, 0.52 mmol) for 4-fluorobenzeneboronic acid, the title compound was obtained as a solid(0.13 g, 70%).

mp: 178~179° C.

$^1$H NMR(CDCl$_3$, 300 MHz): δ8.31 8.29(1H, m), 7.87~7.84(2H, m), 7.76~7.72(1H, m), 7.64~7.61(2H, m), 7.56~7.44(2H, m), 7.22~7.06(2H, m), 6.96~6.93(1H, m), 3.05(3H, s), 2.31(3H, s)

IR(KBr): 2920, 1639, 1465, 1377, 1299, 1149, 771 cm$^{-1}$

EXAMPLE 23

3-(2-Methylphenyl)-2-(4-(methylsulfonyl)phenyl)-4H-1-benzopyran-4-one

Following the procedure of Example 22, Step 3, but replacing m-tolylboronic acid by o-tolylboronic acid, the title compound was obtained as a solid.

mp: 190~191° C.

$^1$H NMR(CDCl$_3$, 300 MHz): δ8.32~8.29(1H, m), 7.86~7.83(2H, m), 7.79~7.74(1H, m), 7.60~7.57(3H, m), 7.51~7.46(1H, m), 7.28~7.26(2H, m), 7.18~7.16(1H, m), 7.01~6.99(1H, m), 3.04(3H, s), 2.15(3H, s)

IR(KBr): 1618, 1376, 1324, 1156, 766 cm$^{-1}$

EXAMPLE 24

3-(3-Chlorophenyl)-2-(4-(methylsulfonyl)phenyl)-4H-1-benzopyran-4-one

Following the procedure of Example 22, Step 3, but replacing m-tolylboronic acid by 3-chlorobenzeneboronic acid, the title compound was obtained as a solid.

mp: 195~196° C.

$^1$H NMR(CDCl$_3$, 300 MHz): δ8.32~8.27(1H, m), 7.91~7.89(2H, m), 7.80~7.74(1H, m), 7.64~7.61(2H, m), 7.58~7.49(2H, m), 7.31~7.28(2H, m), 7.26~7.25(1H, m), 7.07~70.5(1H, m), 3.07(3H, s)

IR(KBr): 1645, 1466, 1377, 1141 cm$^{-1}$

EXAMPLE 25

3-(3-Fluorophenyl)-2-(4-(methylsulfonyl)phenyl)-4H-1-benzopyran-4-one

Following the procedure of Example 22, Step 3, but replacing m-tolylboronic acid by 3-fluorobenzeneboronic acid, the title compound was obtained as a solid.

mp: 225° C.

$^1$H NMR(CDCl$_3$, 300 MHz): δ8.36~8.33(1H, m), 7.91~7.89(2H, m), 7.80~7.73(1H, m), 7.64~7.61(2H, m), 7.58~7.46(2H, m), 7.34~7.28(2H, m), 7.08~6.97(2H, m), 3.07(3H, s)

IR(KBr): 3022, 1646, 1468, 1379, 1296, 1142, 770 cm$^{-1}$

EXAMPLE 26

3-(3-Chloro-4-fluorophenyl)-2-(4-(methylsulfonyl)phenyl)-4H-1-benzopyran-4-one

Following the procedure of Example 22, Step 3, but replacing m-tolylboronic acid by 3-chloro-4-fluorobenzeneboronic acid, the title compound was obtained as a solid.

mp: 196° C.

$^1$H NMR(CDCl$_3$, 300 MHz): δ8.32~8.25(1H, m), 7.94~7.91(2H, m), 7.80~7.75(1H, m), 7.65~7.61(2H, m), 7.58~7.47(2H, m), 7.34~7.31(1H, m), 7.13~7.01(2H, m), 3.08(3H, s)

IR(KBr): 1618, 1466, 1375, 1301, 1144, 761 cm$^{-1}$

EXAMPLE 27

3-(4-Chlorophenyl)-2-(4-(methylsulfonyl)phenyl)-4H-1-benzopyran-4-one

Step 1; 3-(4-Chlorophenyl)-2-(4-(methylthio)phenyl)-4H-1-benzopyran-4-one

Following the procedure of Example 1, Step 5, but substituting 3-bromo-2-(4-(methylthio)phenyl)-4H-1-benzopyran-4-one(0.1 g, 0.29 mmol) for 3-iodo-2-(4-(methylsulfonyl)phenyl) and 4-chlorobenzeneboronic acid (0.05 g, 0.32 mmol) for 4-fluorobenzeneboronic acid, the title compound was obtained as a solid(0.02 g, 20%).

mp: 145~147° C.

$^1$H NMR(CDCl$_3$, 300 MHz): δ8.30~8.26(1H, m), 7.73~7.72(1H, m), 7.55~7.44(3H, m), 7.33~7.29(3H, m), 7.20~7.12(4H, m), 2.48(3H, s)

IR(KBr): 1636, 1594, 1465, 1092 cm$^{-1}$

Step 2; 3-(4-Chlorophenyl)-2-(4-(methylsulfonyl)phenyl)-4H-1-benzopyran-4-one

Following the procedure of Example 1, Step 4, but replacing 3-iodo-2-(4-(methylthio)phenyl)-4H-1-benzopyran-4-one by 3-(4-chlorophenyl)-2-(4-(methylthio)phenyl)-4H-1-benzopyran-4-one(0.05 g, 0.122 mmol), the title compound was obtained as a solid(0.048 g, 89%).

mp: 187~188° C.

$^1$H NMR(CDCl$_3$, 300 MHz): δ8.32~8.28(1H, m), 7.91~7.89(2H, m), 7.79~7.73(1H, m), 7.63~7.61(2H, m), 7.57~7.46(2H, m), 7.34~7.27(2H, m), 7.17~7.14(2H, m), 3.08(3H, s)

IR(KBr): 3083, 2926, 1617, 1465, 1377, 1301, 1157, 1091, 770 cm$^{-1}$

EXAMPLE 28

3-(4-Bromophenyl)-2-(4-(methylsulfonyl)phenyl)-4H-1-benzopyran-4-one

Following the same oxidation procedure of Example 1, Step 4, but replacing 3-iodo-2-(4-(methylthio)phenyl)-4H-1-benzopyran-4-one by 3-(4-bromophenyl)-2-(4-(methylthio)phenyl)-4H-1-benzopyran-4-one (0.06 g, 0.14 mmol), the title compound was obtained as a solid(0.059 g, 90%).

mp: 168~170° C.

$^1$H NMR(CDCl$_3$, 300 MHz): δ8.32~8.28(1H, m), 7.92~7.89(2H, m), 7.77~7.73(1H, m), 7.63~7.46(6H, m), 7.11~7.08(2H, m), 3.08(3H, s)

IR(KBr): 3027, 2925, 1640, 1465, 1375, 1300, 1142, 772 cm$^{-1}$

EXAMPLE 29

2-(4-(Methylthio)phenyl)-3-(4-trifluoromethylphenyl)-4H-1-benzopyran-4-one

Following the procedure of Example 1, Step 5, but substituting 3-bromo-2-(4-(methylthio)phenyl)-4H-1-benzopyran-4-one(0.1 g, 0.32 mmol) for 3-iodo-2-(4-(methylsulfonyl)phenyl)-4H-1-benzopyran-4-one and 4-trifluoromethylbenzeneboronic acid(0.066 g, 0.35 mmol) for 4-fluorobenzeneboronic acid, the title compound was obtained as a solid(0.05 g, 40%).

mp: 189~192° C.

$^1$H NMR(CDCl$_3$, 300 MHz): δ8.31~8.27(1H, m), 7.77~7.70(1H, m), 7.61~7.54(3H, m), 7.49~7.43(1H, m), 7.39~7.36(2H, m), 7.31~7.28(2H, m), 7.15~7.11(2H, m), 2.48(3H, s)

IR(KBr): 2870, 1663, 1425, 1295, 1010 cm$^{-1}$

EXAMPLE 30

2-(4-(Methylsulfonyl)phenyl)-3-(4-trifluoromethylphenyl)-4H-1-benzopyran-4-one

Following the same oxidation procedure of Example 1, Step 4, but replacing 3-iodo-2-(4-(methylthio)phenyl)-4H-

1-benzopyran-4-one by 2-(4-(methylthio)phenyl)-3-(4-trifluoromethylphenyl)-4H-1-benzopyran-4-one(0.027 g,0.065 mmol), the title compound was obtained as a solid (0.03 g, 100%).

mp: 213~216° C.

$^1$H NMR(CDCl$_3$, 300 MHz): δ8.33~8.29(1H, m), 7.92~7.88(2H, m), 7.81~7.75(1H, m), 7.63~7.47(6H, m), 7.37~7.34(2H, m), 3.08(3H, s)

IR(KBr):2927, 1641, 1455, 1378, 1325, 1143, 1109. 1017, 771 cm$^{-1}$

EXAMPLE 31

3-(3,5-Dichlorophenyl)-2-(4-(4-(methylsulfonyl) phenyl)-4H-1-benzopyran-4-one

Step 1; 3-(3,5-Dichloro henyl)-2-(4-(methylthio)phenyl)-4H-1-benzopran-4-one

Following the procedure of Example 1, Step 5, but substituting 3,5-dichlorobenzeneboronic acid(0.067 g, 0.35 mmol) for 4-fluorobenzeneboronic acid and 3-bromo-2-(4-(methylthio)phenyl)-4H-1-benzopyran-4-one(0.1 g, 0.29 mmol) for 3-iodo-2-(4-(methylsulfonyl)phenyl)-4H-1-benzopyran-4-one, the title compound was obtained as a solid(0.043 g, 36%).

mp: 198~200° C.

$^1$H NMR(CDCl$_3$, 300 MHz): δ8.29~8.25(1H, m), 7.77~7.70(1H, m), 7.57~7.43(2H, m), 7.35~7.14(5H, m), 6.94~6.92(1H, m), 6.75~6.74(1H, m), 2.50(3H, s)

IR(KBr): 2880, 1650, 1430, 1253, 950 cm$^{-1}$

Step 2; 3-(3,5-Dichlorophenyl)-2-(4-(metylsulfonyl) phenyl)-4H-1-benzopyran-4-one Following the same oxidation procedure of Example 1, Step 4, but replacing 3-iodo-2-(4-(methylthio)phenyl)-4H-1-benzopyran-4-one by 3-(3,5-dichlorophenyl)-2-(4-(methylthio)phenyl)-4H-1-benzopyran-4-one(0.04 g, 0.096 mmol), the title compound was obtained as a solid(0.02 g, 47%).

mp: 258~260° C.

$^1$H NMR(CDCl$_3$, 300 MHz): δ8.32~8.28(1H, m), 7.97~7.93(2H, m), 7.81~7.75(1H, m), 7.66~7.62(2H, m), 7.59~7.48(2H, m), 7.35~7.33(1H, m), 7.11~7.10(2H, m), 3.08(3H, s)

IR(KBr): 3011, 2920, 1628, 1580, 1453, 1373, 1305, 1299, 1155, 961, 764 cm$^{-1}$

EXAMPLE 32

3-(2-Chloro-5-pyridinyl)-2-(4-(methylsulfonyl) phenyl)-4H-1-benzopyran-4-one and 3-(4-Chloro-3-pyridinyl)-2-(4-(methylsulfonyl)-phenyl)-4H-1-benzopyran-4-one Step 1; 2-(4-(Methylsulfonyl)phenyl)-3-(N-oxo-3-pyridinyl)-4H-1-benzopyran-4-one A solution of 2-(4-(methylsulfonyl)phenyl)-3-(3-pyridinyl)-4H-1-benzopyran-4-one(0.2 g, 0.54 mmol) from Example 15 and MCPBA(0.18 g, 0.6 mmol) in CH$_2$Cl$_2$(20 mL) was refluxed for 1.5 hours. Then the mixture was cooled to room temperature and washed with 1N NaOH solution. The organic layer was dried and concentrated in vacuo to yield the title compound as a pale yellow solid(0.2 g).

mp: 231~232° C.

$^1$H NMR(CDCl$_3$, 300 MHz): δ8.32~8.28(1H, m), 8.18~8.15(1H, m),8.04~8.03(1H, m), 7.99~7.95(2H, m), 7.83~7.76(1H, m), 7.69~7.65(2H, m), 7.60~7.50(2H, m), 7.33~7.21(2H, m), 3.11(3H, s)

IR(KBr): 2923,1641,1467,1385, 1303,1261,1144,760 cm$^{-1}$

Step 2;

compound A: 3-(2-Chloro-5-pyridinyl)-2-(4-(methylsulfonyl)phenyl)-4H-1-benzopyran-4-one compound B: 3-(4-Chloro-3-pyridinyl)-2-(4-(methylsulfonyl)-phenyl)-4H-1-benzopyran-4-one A solution of 2-(4-(methylsulfonyl)phenyl)-3-(N-oxo-3-pyridinyl)-4H-1-benzopyran-4-one(0.2 g, 0.5 mmol) in POCl$_3$(2 mL) was heated at a temperature of 110° C. for 6.5 hours. After evaporating the excess POCl$_3$, the residue was poured into ice and made alkaline with NH$_4$OH and extracted with CH$_2$Cl$_2$. After the solvent being evaporated, the residue was subjected to flash chromatography to yield the title compound as a pale yellow solid(A; 0.092 g, B; 0.03 g).

compound A;

mp: 232~233° C.

$^1$H NMR(CDCl$_3$, 300 MHz): δ8.31~8.28(1H, m), 8.14~8.06(2H, m), 7.96~7.93(2H, m), 7.82~7.75(1H, m), 7.73~7.69(1H, m), 7.64~7.48(4H, m), 7.42~7.36(1H, m), 3.09(3H, s)

IR(KBr): 2920,1647,1465,1308,1140,760 cm$^{-1}$ compound B;

mp: 235~236° C.

$^1$H NMR(CDCl$_3$, 300 MHz): δ8.51~8.49(1H, m), 8.33~8.29(2H, m), 7.92~7.89(2H, m), 7.83~7.76(1H, m), 7.63~7.42(5H, m), 3.06(3H, s)

IR(KBr): 2925,1643,1466,1307,1145,767 cm$^{-1}$

EXAMPLE 33

2-(4-(Methylsulfonyl)phenyl)-3-(2-pyridinyl)-4H-1-benzopyran-4-one

A solution of 3-bromo-2-(4-(methylsulfonyl)phenyl)-4H-1-benzopyran-4-one (0.5 g, 1.32 mmol) from Example 22, Step 2 and 2-tributylstannylpyridine(0.58 g, 1.58 mmol) and tetrakis(triphenylphosphine)palladium(0.15 g, 0.13 mmol) in N-methyl-2-pyrrolidine(50 ml) and ethanol(1 ml) was heated at a temperature of 100° C. for 24 hours. Then the mixture was cooled to room temperature and diluted with ethyl acetate and filtered through a pad of celite. The mixture was washed with 5% aqueous KF, dried and concentrated. The residue was subjected to flash chromatography to yield the title compound as a pale yellow solid(0.27 g).

mp: 203~204° C.

$^1$H NMR(CDCl$_3$, 300 MHz): δ8.55~8.52(1H, m), 8.33~8.29(1H, m),7.88~7.84(2H, m), 7.79~7.73(2H, m), 7.60~7.55(3H, m), 7.51~7.46(2H, m), 7.29~7.24(1H, m), 3.05(3H, s)

IR(KBr): 3058, 1642, 1467, 1382, 1303, 1146, 769 cm$^{-1}$

EXAMPLE 34

6-Fluoro-2-(4-(methylsulfonyl)phenyl)-3-(3-pyridinyl)-4H-1-benzopyran-4-one

Step 1; 5'-Fluoro-2'-hydroxy-4-(methylthio)chalcone

The title compound was prepared from 4-(methylthio) benzaldehyde and 5'-fluoro-2'-hydroxyacetophenone by the same method as described in Step 1 of Example 1.

mp: 147~148° C.

¹H NMR(CDCl₃, 300 MHz): δ7.92(1H, d, J=15.6 Hz), 7.61~7.57(3H, m), 7.50(2H, d, J=15.3 Hz), 7.30~7.21(2H, m), 7.03~6.98(1H, m), 2.54(3H, s)

IR(neat): 1640, 1573, 1482, 1359, 1170, 1097, 776 cm⁻¹

Step 2; 6-Fluoro-2-(4-(methylthio)phenyl)-4H-1-benzopyran-4-one

The title compound was prepared from 5'-fluoro-2'-hydroxy-4-(methylthio)chcalcone and iodine by the same method as described in Step 2 of Example 1.

mp: 177~178° C.

¹H NMR(CDCl₃, 300 MHz): δ7.88~7.81(3H, m), 7.59~7.55(1H, m), 7.45~7.39(1H, m), 7.37~7.33(2H, m), 6.78(1H, s), 2.55(3H, s)

IR(neat): 1639, 1579, 1261,818 cm⁻¹

Step 3; 6-Fluoro-2-(4-(methlsulfonyl)phenyl)-4H-1-benzopyran-4-one

The title compound was prepared from 6-fluoro-2-(4-(methylthio)phenyl)-4H-1-benzopyran-4-one by the same method as described in Step 4 of Example 1.

¹H NMR(CDCl₃, 300 MHz): δ8.16~8.08(4H, m), 7.91~7.87(1H, m), 7.65~7.60(1H, m), 7.51~7.44(1H, m), 6.89(1H, s), 3.12(3H, s)

Step 4; 6-Fluoro-3-iodo-2-(4-(methelsulfonyl)phenyl)-4H-1-benzopran -4-one

A solution of 6-fluoro-2-(4-(methylsulfonyl)phenyl)-4H-1-benzopyran-4-one(3.5 g, 11 mmol), iodine(2.8 g, 11 mmol) and [bis(trifluoroacetoxy)iodo]-benzene (3.5 g, 11 mmol) in CH₂Cl₂(250 ml) was stirred at room temperature for 24 hours. The resulting mixture was washed with saturated Na₂S₂O₃(100 ml), saturated NaHCO₃(100 ml) and then washed with brine and dried over anhydrous MgSO₄ and concentrated. Recrystallization of the resulting residue by CH₂Cl₂ and petroleum ether yielded the title compound as a white solid(2.5 g, 71%).

¹H NMR(CDCl₃, 300 MHz): δ8.14~8.10(2H, m), 8.01~7.91(3H, m),7.55~7.44(2H, m), 3.15(3H, s)

Step 5; 6-Fluoro-2-(4-(methylsulfonyl)phenyl)-3-(3-pyridinyl)-4H-1-benzopyran-4-one The title compound was prepared from 6-fluoro-3-iodo-2-(4-(methylsulfonyl)phenyl)-4H-1-benzopyran-4-one and lithium trimethoxy-3-pyridinylboronate by the same method as described in Step 5 of Example 1.

mp: 233~234° C.

¹H NMR(CDCl₃, 300 MHz): δ8.60~8.54(1H, m), 8.36~8.28(1H, m), 7.96~7.88(3H,m), 7.77~7.73(1H, m), 7.62~7.47(4H, m), 7.40~7.34(1H, m), 3.07(3H, s)

IR(neat): 2928, 1642, 1483, 1272, 1152, 766 cm⁻¹

EXAMPLE 35

6-Fluoro-3-(2-methyl-5-pyridinyl)-2-(4-(methylsulfonyl)-phenyl)-4H-1-benzopyran-4-one Following the procedure of Example 34, Step 5, but substituting lithium trimethoxy-2-methyl-5-pyridinylboronate for lithium trimethoxy-3-pyridinylboronate, the title compound was obtained as a solid.

mp: 145~148° C.

¹H NMR(CDCl₃, 300 MHz): δ8.20~8.19(1H, m), 7.95~7.89(3H, m),7.63~7.45(5H, m), 7.23~7.20(1H, m), 3.08(3H, s), 2.58(3H, s)

IR(KBr): 2925,1613,1451,1315,1150,767 cm⁻¹

EXAMPLE 36

3-(4-Fluorophenyl)-2-(4-(methylsulfonyl)phenyl)-4H-1-benzopyran-4-thione

A solution of 3-(4-fluorophenyl)-2-(4-(methylsulfonyl)phenyl)-4H-1-benzopyran-4-one(0.45 g, 1.14 mmol) from Example 1 and Lawesson's reagent(0.23 g, 0.57 mmol) in toluene(10 ml) was refluxed for 1 hour. The resulting mixture was concentrated and subjected to flash chromatography using a mixture of hexane:ethyl acetate:dichloroethane(1:1:1) as an eluant to yield the title compound as a deep green solid(0.4 g, 85%).

mp: 203~205° C.

¹H NMR(CDCl₃, 300 MHz): δ8.67~8.64(1H, m), 7.88~7.85(2H, d), 7.80~7.75(1H,m), 7.60~7.57(2H, d), 7.55 (1H, s), 7.51~7.46(1H, m), 7.16~7.02(4H, m), 3.06(3H, s)

IR(KBr): 2929, 1605, 1589, 1536, 1508, 1459, 1400, 1377, 1314, 1297, 1254, 1151, 833 cm⁻¹

EXAMPLES 37–46

The inventive compounds of Examples 37–46 were produced by the same procedure described in Example 36, but substituting appropriate benzopyranone for 3-(4-fluorophenyl)-2-(4-(methylsulfonyl)phenyl)-4H-1-benzopyran-4-one. These compounds and their physical properties are shown in Table 2.

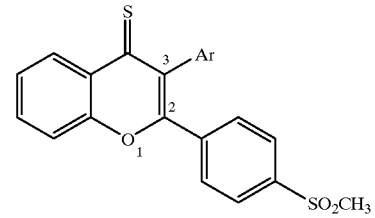

TABLE 2

| Example | 3-Ar | mp (° C.) | ¹H NMR(CDCl₃, 300 MHz); δ | IR(KBr); cm⁻¹ |
| --- | --- | --- | --- | --- |
| 37 | phenyl | 204–206 | 8.68~8.65(1H, m), 7.84~7.81(2H, d), 7.80~7.74(1H, m), 7.60~7.58(2H, d), 7.55(1H, s), 7.50~7.45(1H, m), 7.36~7.34(3H, m), 7.18~7.15(2H, m), 3.04(3H, s) | 2931, 1589, 1455, 1375, 1298, 1150 |
| 38 | 2,3-dichlorophenyl | 191–192 | 8.65~8.63(1H, m), 7.91~7.89(2H, m), 7.82~7.76(1H, m), 7.67~7.64(2H, m), 7.59~7.56(1H, m), 7.52~7.46(2H, m), 7.22~7.16(1H, m), 7.05~7.02(1H, m), 3.06(3H, s) | 1594, 1542, 1457, 1296, 1152 |
| 39 | 3-methylphenyl | 201–202 | 8.68~8.64(1H, m), 7.85~7.82(2H, m), 7.57~7.54(1H, m), 7.49~7.44(1H, m), 7.26~7.16(2H, m), 6.97~6.94(2H, m), | 1607, 1539, 1458, 1374, 1299, 1264, |

TABLE 2-continued

| Example | 3-Ar | mp (° C.) | $^1$H NMR(CDCl$_3$, 300 MHz); δ | IR(KBr); cm$^{-1}$ |
|---|---|---|---|---|
| 40 | 3-chlorophenyl | 196–198 | 3.04(3H, s), 2.30(3H, s)<br>8.64~8.61(1H, m), 7.88~7.85(2H, m),<br>7.77~7.74(1H, m), 7.61~7.55(3H, m),<br>7.50~7.45(1H, m), 7.34~7.24(2H, m),<br>7.17~7.16(1H, m), 7.06~7.03(1H, m),<br>3.05(3H, s) | 1152<br>1589, 1249,<br>1152 |
| 41 | 2-methylphenyl | 234 | 8.68~8.64(1H, m), 7.85~7.82(2H, m),<br>7.81~7.78(1H, m), 7.61~7.58(2H, m),<br>7.51~7.48(1H, m), 7.33~7.16(4H, m),<br>7.01~6.99(1H, m), 3.04(3H, s),<br>2.08(3H, s) | 2913, 1590,<br>1541, 1458,<br>1298, 1253,<br>1150 |
| 42 | 3,4-dichlorophenyl | 168 | 8.65~8.60(1H, m), 7.93~7.90(2H, m),<br>7.82~7.76(1H, m), 7.63~7.60(2H, m),<br>7.58~7.41(3H, m), 7.28(1H, d),<br>7.03~6.99(1H, m), 3.07(3H, s) | 1591, 1463,<br>1139, 1243,<br>1153, 774 |
| 43 | 4-methylphenyl | 204–205 | 8.68~8.64(1H, m), 7.84~7.82(2H, d),<br>7.78~7.73(1H, m), 7.61~7.59(2H, d),<br>7.57~7.44(2H, m), 7.17~7.15(2H, d)<br>7.05~7.02(2H, d), 3.05(3H, s),<br>2.37(3H, s) | 2918, 1593,<br>1370, 1298,<br>1251, 1149 |
| 44 | 4-methoxyphenyl | 199 | 8.68~8.65(1H, d), 7.86~7.83(2H, d),<br>7.78~7.72(1H, m), 7.62~7.59(2H, d),<br>7.56~7.44(2H, m), 7.09~7.06(2H, d),<br>6.89~6.87(2H, d), 3.83(3H, s),<br>3.05(3H, s) | 1590, 1510,<br>1459, 1297,<br>1152 |
| 45 | 2-fluorophenyl | 198–200 | 8.67~8.64(1H, d), 7.88~7.85(2H, d),<br>7.80~7.75(1H, m), 7.66~7.63(2H, d),<br>7.57~7.55(1H, d), 7.50~7.45(1H, t),<br>7.36(1H, m), 7.14~7.06(3H, m),<br>3.05(3H, s) | 3088, 1591,<br>1537, 1465,<br>1460, 1376,<br>1152, 757 |
| 46 | 3-fluorophenyl | 212 | 8.65~8.63(1H, m), 7.87~7.85(2H, m),<br>7.80~7.74(1H, m), 7.63~7.55(3H, m),<br>7.50~7.45(1H, m), 7.36~7.18(1H, m),<br>7.08~7.02(1H, m), 6.96~6.89(2H, m),<br>3.05(3H, s) | 3032, 1591,<br>1297, 1261,<br>1127 |

EXAMPLE 47

2-(4-(Aminosulfonyl)phenyl)-6-fluoro-3-phenyl-4H-1-benzopyran-4-one

Step 1; 3-Bromo-6-fluoro-2-(4-(methylthio)phepnyl)-4H-1-benzopyran-4-one

A solution of 6-fluoro-2-(4-(methylthio)phenyl)-4H-1-benzopyran-4-one(7.43 g, 25.95 mmol) from Example 34, Step 2 and NBS(6.93 g, 38.93, mmol) in CHCl$_3$(100 ml) was refluxed for 20 hours. The resulting mixture was washed with saturated NaHCO$_3$, brine and dried over anhydrous MgSO$_4$. Recrystallization of the resulting residue by CH$_2$Cl$_2$ and petroleum ether yielded the title compound as a solid(7.38 g, 78%).

mp: 228~229° C.

$^1$H NMR(CDCl$_3$, 300 MHz): δ7.93(1H. dd, J=7.8,3.0 Hz), 7.84~7.79(2H, m), 7.5~7.50(1H, m), 7.48~7.41(1H, m), 7.39~7.34(2H, m), 2.56(3H, s)

IR(KBr): 1651, 1477, 1261, 1062, 823 cm$^{-1}$

Step 2; 3-Bromo-6-fluoro-2-(4-(methylsulfinyl)phenyl)-4H-1-benzopyran-4-one

To a solution of 3-bromo-6-fluoro-2-(4-(methylthio)phenyl)-4H-1-enzopyran-4-one(7.3 g, 19.9 mmol) from Step 1 in CH$_2$Cl$_2$(700 ml) was added a solution of MCPBA (4.0 g, 19.9 mmol) in CH$_2$Cl$_2$(200 ml) at a temperature of 0° C. for 2 hours. The solution was washed two times with saturated Na$_2$CO$_3$(100 ml per each) and the organic layer was washed with H$_2$O , brine and dried over anhydrous MgSO$_4$. After the solvent being evaporated, the resulting solid was subjected to flash chromatography using a mixture of ethyl acetate CH$_2$Cl$_2$(1:1) as an eluant to yield the title compound as a solid(6.1 g, 80%).

mp: 172~174° C.

$^1$H NMR(CDCl$_3$, 300 MHz): δ8.05~8.01(2H, m), 7.96~7.93(1H, m), 7.86~7.82(2H, m), 7.57~7.44(2H, m), 2.83(3H, s)

IR(neat): 2988, 1657, 1481, 1275, 1261, 1081 cm$^{-1}$

Step 3; 2-(4-(Aminosulfona )phenyl)-3-bromo-6-fluoro-4H-1-benzopyran-4-one

A solution of 3-bromo-6-fluoro-2-(4-(methylsulfinyl) phenyl)-4H-1-benzopyran-4-one(6.17 g, 16.18 mmol) in TFAA(trifluoroacetic anhydride, 100 ml) was refluxed for 2 hours. The solvent was removed and the resulting residue was coevaporated three times with using a triethylamine/ MeOH solution(50 ml, 1:1) to yield oil. The oil was dissolved in AcOH(100 ml) and treated at room temperature with Cl$_2$ in AcOH(50 ml). After stirring for 2 hours, the solvent was removed and THF(100 ml) was added to the resulting product. After excessive amount of NH$_4$OH solution was added at a temperature of 0° C., the reaction mixture was stirred for 2 hours at room temperature. Water was added and the product was extracted two times with ethyl acetate(100 ml per each). The extract was dried over anhydride MgSO$_4$ and concentrated. Recrystallization of the resulting residue by CH$_2$Cl$_2$ and petroleum ether yielded the title compound as a solid(3.83 g, 60%).

mp: 266~267° C.

$^1$H NMR(CDCl$_3$—MeOH-d$_4$, 300 MHz): δ8.12~8.10 (2H, m), 8.02~7.99(2H, m), 7.92(1H, dd, J=8.1, 3.0 Hz), 7.64~7.51(2H, m)

IR(KBr): 3300, 3236, 1647, 1552, 1481, 1333, 1163, 1081, 755 cm$^{-1}$

Step 4; 2-(4-(Aminosulfonyl)phenyl)-6-fluoro-3-phenyl-4H-1-benzopyran-4-one

Following the procedure of Example 1, Step 5, but substituting benzeneboronic acid(0.056 g, 0.459 mmol) for 4-fluorobenzeneboronic acid and 2-(4-(aminosulfonyl)phenyl)-3-bromo-6-fluoro-4H-1-benzopyran-4-one(0.153 g, 0.38 mmol) for 3-iodo-2-(4-(methylsulfonyl)phenyl)-4H-1-benzopyran-4-one, the title compound was obtained as a solid(0.08 g, 53%).

mp: 265~267° C.

$^1$H NMR(DMSO-$d_6$, 300 MHz): δ8.22~8.19(2H, m), 7.96~7.94(2H, m), 7.82~7.75(1H, m), 7,60(1H, d, J=8.4 Hz), 7.54(2H, bs, NH$_2$), 7.46(1H, m), 7.32~7.19(5H, m)

IR(KBr): 3358, 3268, 3069, 2924, 1691, 1481, 1306, 1164, 750 cm$^{-1}$

EXAMPLES 48–58

The inventive compounds of Examples 48–58 were produced by the same procedure described in Example 47, step 4, but substituting appropriate boronic acid or boronate for benzeneboronic acid and in case of Example 52–58, the requisite starting material, 2-(4-(aminosulfonyl)phenyl)-3-bromo4H-1-benzopyran-4-one was prepared in the same way to 6-fluoro analog from 2-(4-(methylthio)phenyl)-4H-1-benzopyran-4-one. These compounds and their physical properties are shown in Table 3.

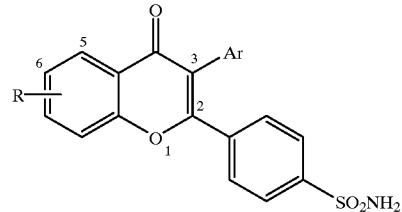

TABLE 3

| Example | 3-Ar | 6-R | mp (° C.) | $^1$H NMR(300 MHz); δ | IR(KBr); cm$^{-1}$ |
|---|---|---|---|---|---|
| 48 | 4-fluorophenyl | F | 224–226 | (DMSO-$d_6$); 7.93(1H, dd, J=8.1, 3.0 Hz), 7.88~7.85(2H, m), 7.59~7.48(4H, m), 7.20~7.16(2H, m), 7.07~7.01(2H, m), 4.86(2H, bs, NH$_2$) | 3408, 3226, 3083, 1631, 1484, 1166, 768 |
| 49 | 4-methylphenyl | F | 215–217 | (CDCl$_3$); 7.91(1H, dd, J=8, 1, 3.0 Hz), 7.84~7.81(2H, m), 7.58~7.53(3H, m), 7.49~7.45(1H, m), 7.15~7.12(2H, m), 7.07~7.05(2H, m), 4.99(2H, bs, NH$_2$) | 3240, 3075, 2924, 1629, 1482, 1343, 1185, 729 |
| 50 | 4-chlorophenyl | F | 215–217 | (CDCl$_3$); 7.92(1H, dd, J=8, 4, 3.0 Hz), 7.89~7.85(2H, m), 7.60~7.45(4H, m), 7.34~7.30(2H, m), 7.16~7.13(2H, m), 4.93(2H, bs, NH$_2$) | 3386, 2629, 1481, 1343, 1118, 1095, 775 |
| 51 | 3-fluorophenyl | F | 257–258 | (CDCl$_3$); 7.92(1H, dd, J=8, 1, 3.0 Hz), 7.61~7.49(4H, m) 7.09~7.02(1H, m), 6.97~6.93(2H, m), 4.86(2H, bs, NH$_2$) | 3413, 3334, 3229, 1638, 1485, 1335, 1273, 1166, 764 |
| 52 | 4-fluorophenyl | H | 267–268 | (CDCl$_3$/MeOH-$d_4$); 8.27(1H, dd, J=8.4 1.8 Hz), 7.88~7.77(3H, s), 7.62~7.48(4H, m), 7.22~7.17(2H, m), 7.07~7.01(2H, m) | 3331, 3219, 1627, 1470, 1338, 1116, 834 |
| 53 | phenyl | H | 218–220 | (CDCl$_3$/MeOH-$d_4$); 8.32~8.29(1H, m), 7.83~7.80(2H, m), 7.75~7.71(3H, m), 7.57~7.43(2H, m), 7.34~7.32(3H, m), 7.21~7.18(2H, m), 4.86(2H, bs, NH$_2$) | 3302, 2929, 1631, 1468, 1344, 1146, 768 |
| 54 | (3,4-methylenedioxy)phenyl | H | 225–223 | (DMSO-$d_6$); 8.14~8.11(1H, m) 7.90~7.52(7H, m), 7.46(2H, brs), 6.35~6.32(2H, m), 6.58(1H, m), 6.03(2H, s) | 3387, 2931, 1615, 1436, 1340, 1243, 1168, 1037, 768 |
| 55 | 4-methoxyphenyl | H | 252–254 | (DMSO-$d_6$); 8.14~8.11(1H, m), 7.89~7.51(7H, m), 7.45(2H, brs), 7.13~7.10(2H, m), 6.90~6.87(2H, m), 3.75(3H, s) | 3315, 3224, 2929, 1600, 1466, 1350, 1238, 1150, 768 |
| 56 | 4-methylthiophenyl | H | 224–226 | (DMSO-$d_6$); 8.14~8.11(1H, m), 7.92~7.52(7H, m), 7.47(2H, brs), 7.21~7.12(4H, m), 2.50(3H, s) | 3333, 2931, 1609, 1467, 1353, 1168, 730 |
| 57 | 3,4-dichlorophenyl | H | 215–217 | (DMSO-$d_6$); 8.16~8.12(1H, m), 7.94~7.40(4H, m), 7.63~7.64(2H, m), 7.60~7.54(3H, m), 7.16~7.12(1H, m), 7.47(2H, brs) | 3302, 2929, 1631, 1463, 1344, 1146, 768 |
| 58 | 2-fluorophenyl | H | 215–217 | (DMSO-$d_6$); 8.15~8.11(1H, m), 7.92~7.88(1H, m), 7.81~7.55(6H, m), 7.48(2H, brs), 7.42~7.36(1H, m), 7.27~7.14(3H, m) | 3317, 3203, 1615, 1432, 1320, 1113, 760 |

EXAMPLE 59

2-(4-(Aminosulfonyl)phenyl)-7-fluoro-3-(4-fluorophenyl)-4H-1-benzopyran-4-one Step 1; 7-Fluoro-3-(4-fluorophenyl)-2-(4-(methylsulfinyl)phenyl)-4H-1-benzopyran-4-one Following the procedure of Example 1, Step 5, but replacing 3-iodo-2-(4-(methylsulfonyl)phenyl)-4H-1-benzopyran-4-one by of 3-bromo-7-fluoro-2-(4-(methylsulfinyl)phenyl)-4H-1-benzopyran-4-one(0.3 g, 0.79 mmol) prepared from 7-fluoro-2-(4-(methylthio)phenyl)-4H-1-benzopyran-4-one in an analogous way to 6-fluoro analog of Step 1, and Step 2 in Example 47, the title compound was obtained(0.26 g, 82%).

$^1$H NMR(CDCl$_3$, 300 MHz): δ8.33~8.30(1H, m), 7.70~7.63(2H, m), 7.50~7.43(2H, m), 7.61(1H, brs), 7.28~7.25(1H, m), 7.23~7.16(2H, m), 7.05~6.99(2H, m), 2.73(3H, s)

Step 2; 2-(4-(Aminosulfonyl)phenyl)-7-fluoro-3-(4-fluorophenyl)-4H-1-benzopyran-4-one Following the procedure of Example 47, Step 3, but substituting 7-fluoro-3-(4-fluorophenyl)-2-(4-(methylsulfinyl)phenyl)-4H-1-benzopyran-4-one(0.18 g, 0.454 mmol) for 3-bromo-6-fluoro-2-(4-(methyl-sulfinyl)phenyl)-4H-1-benzopyran-4-one, the title compound was obtained as a solid(0.07 g, 37%).

mp: 214~215° C.

$^1$H NMR(CDCl$_3$, 300 MHz): δ8.34~8.29(1H, m), 7.88~7.85(2H, m), 7.55~7.52(2H, m), 7.25~7.15(4H, m), 7.07~7.01(2H, m), 4.94(2H, s)

EXAMPLE 60

2-(4-(Aminosulfonyl)phenyl)-7-fluoro-3-(2-fluorophenyl)-4H-1-benzopyran-4-one The title compound was prepared from 7-fluoro-3-(2-fluorophenyl)-2-(4-(methylsulfinyl)phenyl)-4H-1-benzopyran-4-one according to the procedure described in Example 59, Step 2.

mp: 188° C.

$^1$H NMR(CDCl$_3$, 300 MHz): δ8.34~8.29(1H, m), 7.87~7.85(2H, m), 7.59~7.56(2H, m), 7.40~7.32(1H, m), 7.25~7.02(5H, m), 4.96(2H, s)

EXAMPLE 61

2-(4-(Aminosulfonyl)phenyl)-7-fluoro-3-(3-fluorophenyl)-4H-1-benzopyran-4-one The title compound was prepared from 7-fluoro-3-(3-fluorophenyl)-2-(4-(methylsulfinyl)phenyl)-4H-1-benzopyran-4-one according to the procedure described in Example 59, Step 2.

mp: 239~240° C.

$^1$H NMR(DMSO-d$_6$, 300 MHz): δ8.26~8.21(1H, m),7.85~7.82(2H, m), 7.58~7.55(2H, m), 7.47~7.44(1H, m), 7.38(2H, s), 7.36~7.28(2H, m), 7.11~6.97(3H, m)

EXAMPLE 62

2-(4-(Aminosulfonyl)phenyl)-7-fluoro-3-(3,4-dichlorophenyl)-4H-1-benzopyran-4-one The title compound was prepared from 7-fluoro -3-(3,4-dichlorophenyl)-2-(4-(methylsulfinyl)phenyl)-4H-1-benzopyran-4-one according to the procedure described in Example 59, Step 2.

mp: 190~191° C.

$^1$H NMR(CDCl$_3$, 300 MHz): δ8.33~8.28(1H, m), 7.91~7.89(2H, m), 7.57~7.54(2H,m), 7.41~7.37(2H, m), 7.23~7.19(2H, m), 7.00~6.97(1H, m), 4.98(2H, s)

EXAMPLE 63

2-(4-Aminosulfonyl)phenyl-6-methoxy-3-(4-fluorophenyl)-4H-1-benzopyran-4-one The title compound was prepared from 2-(4-aminosulfonyl)phenyl-3-bromo-6-methoxy-4H-1-benzopyran-4-one according to the procedure described in Example 47, Step 4.

$^1$H NMR(CDCl$_3$, 300 MHz): δ7.87(2H, m), 7.54~7.53 (2H, m),7.51~7.37(2H, m),7.22~7.00(5H, m), 4.90(2H, s), 4.01(3H, s)

EXAMPLE 64

2-(4-(Aminosulfonyl)phenyl)-7-methoxy-3-(4-fluorophenyl)-4H-1-benzopyran-4-one The title compound was prepared from 2-(4-(aminosulfonyl)-phenyl)-3bromo-7-methoxy-4H-1-benzopyran-4-one according to the procedure described in Example 47, Step 4.

mp: 245° C.

$^1$H NMR(CDCl$_3$, 300 MHz): δ8.21~8.18(1H, m), 7.87~7.85(2H, m), 7.62~7.60(2H, m),7.22~7.05(6H, m),4.87(2H, s), 4.09(3H, s)

EXAMPLE 65

2-(4-(Aminosulfonyl)phenyl)-8-chloro-3-(4-fluorophenyl)-5-methoxy-4H-1-benzopyran-4-one The title compound was prepared from 2-(4-(aminosulfonyl)phenyl)-3-bromo-8-chloro-5-methoxy-4H-1-benzopyran-4-one according to the procedure described in Example 47, Step 4.

mp: 279~281° C.

$^1$H NMR(DMSO-d$_6$, 300 MHz): δ7.96(1H, dd, J=9.0, 1.2 Hz), 7.79~7.76(2H, m), 7.59~7.42(3H, m), 7.46(2H, bs, NH2), 7.25~7.14(4H, m), 3.84(3H, s)

IR(KBr): 3290, 3220, 1627, 1467, 1416, 1320, 1226, 1162, 1037, 815 cm$^{-1}$

EXAMPLE 66

2-(4-(Aminosulfonyl)phenyl)-8-chloro-3-(4-fluorophenyl)-5-hydroxy-4H-1-benzopyran-4-one To a solution of 2-(4-(aminosulfonyl)phenyl)-8-chloro-3-(4-fluorophenyl)-5-methoxy-4H-1-benzopyran-4-one(0.03 g, 0.07 mmol) in CH$_2$C$_2$(5 ml) was added 1.0M BBr$_3$(0.2 ml) at a temperature of 0° C. The mixture was stirred for 4 hours at room temperature and diluted with CH$_2$Cl$_2$(10 ml). After being washed with water and brine, the solution was dried over anhydrous MgSO$_4$. The crude product was purified by flash chromatography to yield the title compound as a solid(0.02 g, 74%).

mp: 251~252° C.

$^1$H NMR(DMSO-d$_6$, 300 MHz): δ7.93(1H, d, J=9.3 Hz), 7.81~7.78(2H, m), 7.62~7.60(2H, m), 7.48(2H, bs, NH$_2$), 7.32~7.18(5H, m)

IR(KBr): 3311,3234, 1639,, 1592, 1434, 1223, 1167, 712 cm$^{-1}$

EXAMPLE 67

2-(4-(Aminosulfonyl)phenyl)-6-hydroxy-3-(4-fluorophenyl)-4H-1-benzopyran-4-one The title compound was prepared from 2-(4-(aminosulfonyl)phenyl)-6-methoxy-3-(4-fluorophenyl)-4H-1-benzopyran-4-one according to the procedure described in Example 66.

$^1$H NMR(CDCl$_3$, 300 MHz): δ7.88~7.84(2H, m), 7.73~7.70(2H, m),7.60~7.51(3H, m),7.45(1H, s),7.21~7.16 (2H, m),7.09~7.02(2H, m), 4.92(2H, s)

EXAMPLE 68

2-(4-(Aminosulfonyl)phenyl)-6-fluoro-3-(4-fluorophenyl)-4H-1-benzopyran-4-thione The title compound was prepared from 2-(4-(aminosulfonyl)phenyl)-6-fluoro-3-(4-fluorophenyl)-4H-1-benzopyran-4-one according to the procedure described in Example 36.

mp: 224~225° C. $^1$H NMR(CDCl$_3$, 300 MHz): δ8.32(1H, dd, J=8,4,3.0 Hz), 7.85~7.82(2H, m), 7.82~7.47(4H, m), 7.15~7.11(2H, m), 7.08~7.02(2H, m), 5.30(2H, bs, NH$_2$)

IR(KBr): 3370, 3278, 1597, 1493, 1342, 1258, 1159, 1086, 768 cm$^{-1}$

EXAMPLE 69

2-(4-(Aminosulfonyl)phenyl)-3-(4-fluorophenyl)-4H-1-benzopyran-4-thione

The title compound was prepared from 2-(4-(aminosulfonyl)phenyl)-3-(4-fluorophenyl)-4H-1-benzopyran-4-one according to the procedure described in Example 36.

mp: 197~199° C.

$^1$H NMR(CDCl$_3$—MeOH-d$_4$, 300 MHz): δ8.67~8.63 (1H, m), 7.84~7.75(3H, m), 7.59~7.46(5H, m), 7.16~7.12 (2H, m), 7.06~7.01(2H, m)

IR(KBr): 3265, 1590, 1536, 1339, 1250, 1154, 1069, 832 cm$^{-1}$

Experimental Example 1

Regarding the compounds in the above Examples and indomethacin, the inhibition efficacy of COX-2 and COX-1 are being measured by the following two methods. And the results of the inhibition efficacy of COX-2 and COX-1 are shown in Table 4.

1. Evaluation of COX-2's Inhibition Efficacy (J. Pharmacol. Exp. Ther. 166,96(1969))

After cleaning C57BL/6 mouse's abdomen by 70% EtOH, the skin of mouse's abdomen was eliminated cautiously not to harm peritomeum and 5 ml of cold PBS was poured into the abdominal cavity and in certain times later macrophage-bleeding abdominal-liquid was collected by syringe. By adding RPMI-1640 badge containing penicillin (100 unit/mt) and streptomycin(100 mg/ml) to cell pellet obtained by centrifugation of collected liquid about 5 minutes in 1500 rpm, it was disperesed and also COX-1 existing in the cell was inactivated by treating with 500 μM aspirin. After putting 1 ml cell suspension having cell number of 1×10$^6$ cells/mu into each 24-well microtiter plates, macrophages were adhered to the bottom of plate by culturing in the condition of 5% CO$_2$/95% O$_2$, at a temperature of 37° C. for 2 hours. Other cells not being adhered to were eliminated by washing two times with PBS. The purity of macrophages obtained through this process was identified by differential counting. After adding RPMI-1640 badge(normally 5×10$^5$ cell/ml) containing 3% right fetal blood serum to macrophage and treating it with LPS(lipopolysaccharide) to make final concentration as 10 μg/ml, it was cultured in the condition of 5% CO$_2$, at a temperature of 37° C. for 16 hours. After inducing COX-2 by LPS, the cell culture medium was eliminated and macrophages was washed two times with PBS. And 1 ml of RRPI-1640 badge was added to each well again and after treating them with sample with appropriate concentration, they were cultured at a temperature of 37$_i$ É for 10 minutes. And then treated them with arachidonic acid to make their final concentration as 10 μM and cultured them additional 10 minutes, all the supernatant liquid of reaction was obtained. The amount of PGE$_2$ produced in the supernatant liquid of reaction was determined by the PGE$_2$ radioimmuno assay. The 100% COX-2's activation is referenced by the difference of the amount of PGE$_2$ produced in the supernatant liquid of reaction between with 10 μM arachidonic acid treatment and without 10 μM arachidonic acid treatment.

2. Evaluation of COX-1's Inhibition Efficacy

Following the same procedure as the above evaluation of COX-2's inhibition efficacy, but there is no pre-treatment of aspirin and LPS in the adhesion of macrophage.

TABLE 4

| | Inhibition (%) | | | | | | Inhibition (%) | | | | |
|---|---|---|---|---|---|---|---|---|---|---|---|
| | COX-2 (μg/ml) | | | COX-1 (μg/ml) | | | COX-2 (μg/ml) | | | COX-1 (μg/ml) | |
| Example | 10 | 1 | 0.1 | 10 | 1 | Example | 10 | 1 | 0.1 | 10 | 1 |
| 1 | | 100 | 94 | <5 | | 39 | 86 | 31 | 11 | | |
| 2 | 81 | 68 | 34 | <5 | | 40 | 69 | 29 | 6 | <5 | |
| 3 | 72 | 61 | 13 | | | 41 | 96 | 36 | <5 | <5 | |
| 4 | 5< | | | <5 | | 46 | 91 | 67 | 4 | | |
| 5 | 100 | 90 | 39 | | | 47 | | 86 | 23 | | |
| 6 | 100 | 92 | 42 | | | 48 | | 100 | 63 | 48 | 36 |
| 9 | 29 | 5< | | <5 | | 49 | 92 | 76 | 32 | | |
| 10 | 86 | 67 | 14 | <5 | | 50 | 87 | 80 | 5 | | |
| 11 | | 89 | 46 | <5 | | 51 | 100 | 83 | 56 | 6 | |
| 14 | 71 | 32 | 18 | | | 52 | 99 | 96 | 73 | 67 | 62 |
| 15 | 90 | 83 | | 13 | | 53 | 92 | 90 | 76 | 61 | 52 |
| 16 | 24 | | | <5 | | 54 | | 84 | 20 | 75 | |

TABLE 4-continued

| | Inhibition (%) | | | | | | Inhibition (%) | | | | |
| --- | --- | --- | --- | --- | --- | --- | --- | --- | --- | --- | --- |
| | COX-2 (μg/ml) | | | COX-1 (μg/ml) | | | COX-2 (μg/ml) | | | COX-1 (μg/ml) | |
| Example | 10 | 1 | 0.1 | 10 | 1 | Example | 10 | 1 | 0.1 | 10 | 1 |
| 17 | 13 | | <5 | | | 55 | 100 | 90 | | 84 | 66 |
| 18 | 86 | 51 | | 18 | | 56 | 90 | 84 | 53 | 90 | 77 |
| 19 | 35 | 18 | | 11 | | 57 | | 96 | 48 | 75 | |
| 20 | 85 | <5 | | <5 | | 58 | 96 | 63 | | 60 | 34 |
| 21 | 55 | 35 | | <5 | | 59 | | 100 | 39 | | |
| 22 | 90 | 82 | 14 | | | 60 | | 100 | 43 | | |
| 23 | 97 | 84 | 23 | | | 61 | | 97 | 69 | 38 | 22 |
| 24 | 95 | 86 | 22 | | | 62 | | 100 | 89 | 76 | 54 |
| 33 | 44 | 27 | | 17 | | 64 | 47 | 52 | <5 | | |
| 34 | 78 | 66 | | 12 | | 65 | 93 | 67 | | 73 | 24 |
| 36 | 100 | 80 | 56 | <5 | | 66 | 90 | 83 | | 80 | 40 |
| 37 | 88 | 76 | 47 | <5 | | 68 | | 100 | 89 | 83 | 58 |
| 38 | 96 | 77 | 18 | | | 69 | 100 | 98 | 42 | 90 | 68 |

Experimental Example 2

Regarding the compounds in some of the above Examples and indomethacin, depressant action on edema in mouse's ear and depressant action on edema in mouse's foot being induced by carrageenan are being measured by the following 2 methods. And the results of the depressant action on edema in mouse's ear and depressant action on edema in mouse's foot being induced by carrageenan are shown in Table 5.

1. Measurement of Depressant Action on Edama in Mouse's Ear

At 30 minutes after coating the left ear of ICR mouse, weighing 20 g, with a solution of appropriate amount of sample in 20 μl of mixed solvent DMSO:acetone(1:9), 25 μg of TPA(tetradecanoylphorbol acetate) was coated on both ears. The determination of depressant action on edema was made in 5 hours later by the number of neutral granulocyte gathering in the ear after inducing TPA inflammation. The number of neutral granulocyte was estimated by measuring the activation of myeloperoxidase.

2. Measurement of Depressant Action on Edama in Mouse's Foot Induced by Carrageenan At 1 hour after oral administering to Male-Sprague-Dawley-white mouse, weighing 150~200 g, with a suspended solution of appropriate amount of sample in 0.5% of carboxymethyl cellulose and 0.2% of TWEEN solution, edema on the right foot of mouse was induced by injecting 0.1 ml(1%) of carrageenan-saline solution. Right after the inducement of edema by carrageenan and 3 hours later, the edema rate was estimated by measuring white mouse's foot volume with Displacement Plethysmometer(Ugo Basile, Italy). Carrageenan injection Drug was administered 1 hour before the carrageenan injection. Depressant rate of edema is produced by the following equation 1.

% Depressant rate of edema=(1−$\Delta$Vtreated group/$\Delta$Vcontrol group)×100 $\Delta$ V: change of foot volume   [Equation 1]

TABLE 5

| | depressant rate of ear edema (ED50, % depressant rate) | depressant rate of edema rate induced by carrageenan (oral administration) (ED50, % depressant rate) |
| --- | --- | --- |
| indomethacine | 0.4 mg/ear, ED50 | 4.3 mg/kg, ED50 p.o. |
| Example 1 | 0.4 mg/ear, ED50 | 50 mg/kg, 43% depression |
| Example 2 | — | — |
| Example 3 | 1.2 mg/ear, ED50 | 50 mg/kg, 52% depression |
| Example 5 | — | — |
| Example 6 | — | 50 mg/kg, 37% depression |
| Example 10 | 0.6 mg/ear, ED50 | — |
| Example 11 | — | 30 mg/kg, 17% depression |
| Example 12 | 0.4 mg/ear, ED50 | 30 mg/kg, 20% depression |
| Example 14 | — | — |
| Example 15 | — | 30 mg/kg, 41% depression |
| Example 26 | 0.6 mg/ear, ED50 | 50 mg/kg, 23% depression |
| Example 27 | — | — |
| Example 28 | 0.8 mg/ear, ED50 | — |
| Example 34 | | 3 mg/kg, 23% depression |
| Example 36 | 1.0 mg/ear, ED50 | 30 mg/kg, 20% depression |
| Example 37 | | 30 mg/kg, 16% depression |

As can be seen from the above Table 4, the compound(I) of the present invention has high selectivity on COX-2 so that it could inhibit the action of COX-2.

The present invention relates to the cyclooxygenase-2 inhibitor composition having one or more of which is selected from non-toxic, pharmaceutically acceptable carrier or adjuvant or diluent or other activating components with pharmaceutically effective amount of compound(I), and the composition of the present invention may be oil or could be in the form of solution. suspension or emulsion in aqueous medium or could be in the form of powder that is melted in sterile and pyrogen-free water before being used as oral formulation or parenteral formulation such as hypodermic injection, vein injection, intramuscular injection, sternal injection. suppository or cream or gel or ointments or local formulation such as suspension, mouth washing.

In case of oral formulation, the composition of the present invention is prepared by the disclosed method of employing pharmaceutically acceptable carrier and excipient, for example, in the form of tablet, troches, saccharated tablet, aqueous or oily suspension, dispersive powder or particle, emulsion, soft or hard capsule, syrup, elixir, and it's stored by unit dosage or in multicapacity container.

The tablet, one of oral formulation, has the compound of the present invention mixed inactive additives which could be used in the preparation of tablet. The example may include, but not limited to, excipients such as calcium carbonate, sodium carbonate, lactose, calcium phosphate, sodium phosphate or pelletizing agents such as corn, starch, alginic acid or disintegrating agents or coupling agents such as starch, gelatin, acacia or lubricants such as magnesium stearate, stearic acid, talc. The tablet is used without coating, or is used with coating to prevent absorption in gastrointestinal and disintegration of tablet. For example, time inhibitors such as glyceryl-mono-stearate or glyceryl-di-stearate is applicable. Hard capsule is a mixture of the compound of the present invention with solid diluent such as calcium carbonate, calcium phosphate. kaolin, and soft capsule is a mixture of the compound of the present invention with active components, which are mixtures of solvents such as water, mixable polyethyleneglycol, PEGs, ethanol with oil solvents such as peanut oil, liquid paraffin, olive oil.

Liquid suspensions is a mixture of active components with excipients, which is appropriate for preparation of liquid suspension. Excipinet for liquid suspensions is, for example, suspensions such as sodium carboxymethyl cellulose, methyl cellulose, hydroxy-propylmethyl cellulose, sodium alginic acid, polyvinyl-pyrrolidone, gum tragacanth, gum acacia or polyoxylenestearate which is a condensate of fatty acid and alkylene oxide or heptadeca-ethyleneoxycetanol which is a condensate of long fatty acid and alkylene oxide; polyoxyethylenesorbitolmonoolate which is a condensate of hexitol anhydride and ester derived from fatty acid and ethylene oxide or humectants or dispersing agents. Liquid suspensions may further contain preservatives, colorants, condiments, sweeteners.

Oil suspensions is a mixture of vegetable oil such as olive oil, sesami oil or mineral oil such as liquid paraffin with active components, for example, it contains thickening agents such as beeswax, soft paraffin, cetyl alcohol. Also it contains preservatives, colorants, condiments, sweeteners, but such composition may contain antioxidants such as vitamin-c to improve shelf life.

Dispersive powder or particle contains active component in a mixture of dispersing agents, humectants, suspending agents and preservatives. The example of an adequate dispersing agent is humectants and suspending agents which are mentioned above. Additional excipient, for example, is sweeteners, condiments, colorants and etc.

Water in oil emulsion is a mixture of oil phase like vegetable oil such as olive oil or mineral oil such as liquid paraffin with emulsifier like natural phospholipid such as soy bean lecithin or sorbitanmonoolate, which is derived from hexitol anhydride or fatty acid ester, or reoxyethylenesorbitolmonoolate which is a condensate of hexitol anhydride and ester derived from fatty acid and ethylene oxide.

Syrup and elixir is a mixture of sweetener such as glycerol, propyleneglycol, sorbitol, sucrose with active components.

Parenteral formulation is injected in the form of suspension which is a mixture of sterile injectable solution or non-toxic, pharmaceutically acceptable diluting agents or solvents sucha as 1,3-butane-diol with active component. Available excipient or solvents is, for example, water, Ringer's solution and isotonic sodium chloride solution. Cosolvent such as ethanol, polyethyleneglycol, polyprolyleneglycol is also available. Also, bland fixed oil could be commonly used as a solvent or a suspending solvent. And bland fixed oil for this purpose is used with synthetic mono-, di- glyceride. Also, fatty acid like oleic acid could be used in the preparation of injection. Suppository form is prepared by mixing with appropriate bland excipients such as cocoa butter and polyethyleneglycol, which keep suppository as solid form at room temperature and make suppository melt inside rectum. It is administered through rectum.

Local formulation generally consists of pharmaceutical carrier. auxiliary solvent, emulsifier, penetration accelerant, preservative and palliative.

In case of treating diseases with composition of the present invention, the dosage of active component of compound(I) depends on the patient's age, weight, general health condition, sex, meal, administration time, evacuation speed, drug combination, and severity of disease during treatment, but it could be used in the range of 0.01~140 mg per 1 kg(weight) per day according to the kind of diseases, or 0.5 mg~7 g per patient. For example, inflammation could be effectively treated with administering 0.01~50 mg per 1 kg(weight) or 0.5mg~3.5 g per patient.

On the one hand, the amount of the compound of the present invention which would be mixed with carrier material to decide one formulation is different according to the way of administration paths and treating patients. For example, in formulation for oral administration to human, it consists of 5~95% of carrier materials and 0.5 mg~5 g of active components and in formulation for parenteral administration to human, it consists of 5~99% of carrier materials and 0.1 mg~2.5 g of active components in the oral administration.

It is understood that the foregoing detailed description is given merely by way of illustration and that modifications and variations may be therein without departing from the spirit and scope of the invention.

What is claimed is:

1. A compound represented by the following formula(I):

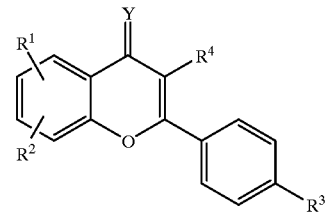

(I)

wherein

Y is an oxygen atom or a sulfur atom;

$R^1$ and $R^2$, identical to or different from each other, are independently a hydrogen atom, a halogen atom, a $C_1$–$C_6$ lower alkyl group, a trifluoromethyl group, an alkoxy group, a hydroxy group, a nitro group, a nitrile group, or a carboxyl group;

$R^3$ is a group of a formula: $S(O)nR^5$ wherein n is an integer of 0~2, $R^5$ is a hydrogen atom, a $C_1$–$C_6$ lower alkyl group, or a group of a formula: $NR^6R^7$ wherein $R^6$ and $R^7$, identical to or different from each other, are Independently a hydrogen atom, or a $C_1$–$C_6$ lower alkyl group; and $R^4$ is oxazolyl, benzo[b]thienyl, furanyl, thienyl, naphthyl, thiazolyl, indolyl, pyrolyl, benzofuranyl, pyrazolyl, pyrazolyl substituted with a $C_1$–$C_6$ lower alkyl group, indanyl, pyrazinyl, or a substituted group presented by the following structures:

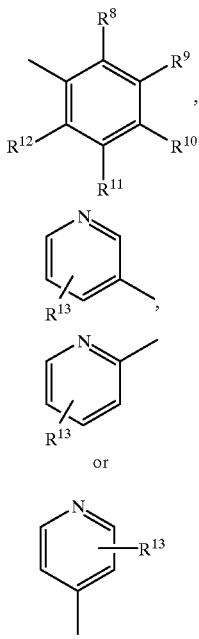

wherein
R[8] through R[12], identical to or different from one another, are independently a hydrogen atom, a halogen atom, a $C_1$–$C_6$ lower alkyl group, a trifluoromethyl group, an alkoxy group, a hydroxy group, a hydroxyalkyl group, a nitro group, a 3,4-methylenedioxy group, a group of a formula: $S(O)nR^5$, a group of a formula: $NR^6R^7$, a trifluoromethoxy group, a nitrile group, a carboxyl group, an acetyl group, or a formyl group wherein n, $R^5$, $R^6$ and $R^7$ have the same meaning as defined by $R^3$ above; and $R^{13}$ is a hydrogen atom, a halogen atom, a $C_1$–$C_6$ lower alkyl group, a trifluoromethyl group, a alkoxy group, a hydroxy group, a trifluoromethoxy group, a carboxyl group, or an acetyl group;

or a pharmaceutically acceptable salt thereof.

2. The compound (I) according to claim 1, which is
2-(4-(Methylsulfonyl)phenyl)-3-phenyl-4H-1-benzopyran-4-one,
2-(4-(Methylsulfonyl)phenyl)-3-(4-(methylthio)phenyl)-4H-1-benzopyran-4-one,
3-(2-Methoxyphenyl)-2-(4-(methylsulfonyl)phenyl)-4H-1-benzopyran-4-one,
3-(4-Fluorophenyl)-2-(4-(methylsulfonyl)phenyl)-4H-1-benzopyran-4-one,
3-(2-Chlorophenyl)-2-(4-(methylsulfonyl)phenyl)-4H-1-benzopyran-4-one,
3-(4-(N,N-Dimethylamino)phenyl)-2-(4(methylsulfonyl)phenyl)-4H-1-benzopyran-4-one,
3-(4-(N-Methylamino)phenyl)-2-(4-(methylsulfonyl)phenyl)-4H-1-benzopyran-4-one,
2-(4-(Methylsulfonyl)phenyl)-3-(4-trifluoromethoxyphenyl)-4H-1-benzopyran-4-one,
3-(3-Methoxyphenyl)-2-(4-(methylsulfonyl)phenyl)-4H-1-benzopyran-4-one,
3-(4-isopropylphenyl)-2-(4-(methylsulfonyl)phenyl)-4H-1-benzopyran-4-one,
3-(4-Ethylphenyl)-2-(4-(methylsulfonyl)phenyl)-4H-1-benzopyran-4-one,
3-(4-Hydroxymethylphenyl)-2-(4-(methylsulfonyl)phenyl)-4H-1-benzopyran-4-one,
2-(4-(Methylsulfonyl)phenyl)-3-(4trifluoromethylphenyl)-4H-1-benzopyran-4-one,
3-(4-Hydroxyphenyl)-2-(4(methylsulfonyl)phenyl)-4H-1-benzopyran-4-one,
3-(2,3-Difluorophenyl)-2-(4-(methylsulfonyl)phenyl)-4H-1-benzopyran-4-one,
3-(3,5-Difluorophenyl)-2-(4-(methylsulfonyl)phenyl)-4H-1-benzopyran-4-one,
3-(2-Hydroxyphenyl)-2-(4-(methylsulfonyl)phenyl)-4H-1-benzopyran-4-one,
3-(2,4-Difluorophenyl)-2-(4-(methylsulfonyl)phenyl)-4H-1-benzopyran-4-one,
3-(4-Methylphenyl)-2-(4-(methylsulfonyl)phenyl)-4H-1-benzopyran-4-one,
3-(2,4-Dichlorophenyl)-2-(4-(methylsulfonyl)phenyl)-4H-1-benzopyran-4-one,
3-(4-Acetylphenyl)-2-(4-(methylsulfonyl)phenyl)-4H-1-benzopyran-4-one,
3-(2,4-Dimethylphenyl)-2-(4-(methylsulfonyl)phenyl)-4H-1-benzopyran-4-one,
3-(4-Formylphenyl)-2-(4-(methylsulfonyl)phenyl)-4H-1-benzopyran-4-one,
3-(4-Carboxyphenyl)-2-(4-(methylsulfonyl)phenyl)-4H-1-benzopyran-4-one,
3-(4-Chloro-3-fluorophenyl)-2-(4-(methylsulfonyl)phenyl)-4H-1-benzopyran-4-one,
3-(4-Methoxyphenyl)-2-(4-(methylsulfonyl)phenyl)-4H-1-benzopyran-4-one,
3-(3,4-Dichlorophenyl)-2-(4-(methylsulfonyl)phenyl)-4H-1-benzopyran-4-one,
3-(2-Fluorophenyl)-2-(4-(methylsulfonyl)phenyl)-4H-1-benzopyran-4-one,
3-(4-Fluorophenyl)-5-methoxy-2-(4-(methylsulfonyl)phenyl)-4H-1-benzopyran-4-one,
3-(4-Fluorophenyl)-5-hydroxy-2-(4-(methylsulfonyl)phenyl)-4H-1-benzopyran-4-one,
3-(3,5-Dichlorophenyl)-2-(4-(methylsulfonyl)phenyl)-4H-1-benzopyran-4-one,
3-(N-methyl-3-pyrazolyl)-2-(4-(methylsulfonyl)phenyly)-4H-1-benzopyran4-one,
3-(4-Chlorophenyl)-2-(4-(methylsulfonyl)phenyl)-4H-1-benzopyran-4-one,
6-Chloro-3-(4-fluorophenyl)-2-(4-(methylsulfonyl)phenyl)-4H-1-benzopyran-4-one,
2-(4(methylsulfonyl)phenyl)-3-(3-nitrophenyl)-4H-1-benzopyran-4-one,
3-(3,4-Difluorophenyl)-2-(4-(methylsulfonyl)phenyl)-4H-1-benzopyran-4-one,
2-(4-(methylsulfonyl)phenyl)-3-(1-naphthyl)-4H-1-benzopyran 4-one,
3-(3-Methylphenyl)-2-(4(methylsulfonyl)phenyl)-4H-1-benzopyran-4-one,
3-(2-Methylphenyl)-2-(4-(methylsulfonyl)phenyl)-4H-1-benzopyran-4-one,
3-(3-Chloro-4-fluorophenyl)-2-(4-(methylsulfonyl)phenyl)-4H-1-benzopyran-4-one,
3-(4Bromophenyl)-2-(4-(methylsulfonyl)phenyl)-4H-1-benzopyran-4-one,
3-(2,3-Dichlorophenyl)-2-(4-(methylsulfonyl)phenyl)-4H-1-benzopyran-4-one,
3(3-Fluorophenyl)-2-(4-(methylsulfonyl)phenyl)-4H-1-benzopyran-4-one,
3-(3-Chlorophenyl)-2-(4(methylsulfonyl)phenyl)-4H-1-benzopyran-1-one,
2-(4-(Methylsulfonyl)phenyl)-3-(2-oxazolyl)-4H-1-benzopyran-4-one,
6-Fluoro-2-(4-fluorophenyl)-3-(4-(methylsulfonyl)phenyl)-4H-1-benzopyran-4-one, 3-(2-Benzo[b]thienyl)-2-(4-(methylsulfonyl)phenyl)-4H-1-benzopyran-4-one,
3-(2-Chloro-5-pyridinyl)-7-fluoro-2-(4-(methylsulfonyl)phenyl)-4H-1-benzopyran-4-one,
7-Fluoro-2-(4-(methylsulfonyl)phenyl)-3-(3-pyridinyl)-4H-1-benzopyran-4-one,
2-(4-(Methylsulfonyl)phenyl)-3-(2-pyridinyl)-4H-1-benzopyran-4-one,
2-(4-(Methylsulfonyl)phenyl)-3-(3-pyridinyl)-4H-1-benzopyran-4-one,
2-(4-(Methylsulfonyl)phenyl)-3-(4-pyridinyl)-4H-1-benzopyran-4-one,
6-Fluoro-2-(4-(methylsulfonyl)phenyl)-3-(3-pyridinyl)-4H-1-benzopyran-4-one,
7-Fluoro-3-(2-methoxy-5-pyridinyl)-2-(4-(methylsulfonyl)phenyl)-4H-1-benzopyran-4-one,
3-((3,4-methylenedioxy)phenyl)-2-(4-(methylsulfonyl)phenyl)-4H-1-benzopyran-4-one,
2-(4-(Methylsulfonyl)phenyl)-3-(2-thiazolyl)-4H-1-benzopyran-4-one,
3-(Benzofuran-2-yl)-2-(4-(methylsulfonyl)phenyl)-4H-1-benzopyran-4-one,
2-(4-(Methylsulfonyl)phenyl)-3-(2-thienyl)-4H-1-benzopyran-4-one,
2-(4-(Methylsulfonyl)phenyl)-3-(2-pyrazinyl)-4H-1-benzopyran-4-one,
3-(2-Methyl-5-pyridinyl)-2-(4(methylsulfonyl)phenyl)-4H-1-benzopyran-4-one,
3-(2-Methoxy-5-pyridinyl)-2-(4-(methylsulfonyl)phenyl)-4H-1-benzopyran-4-one,
6-Fluoro-3-(2-methyl-5-pyridinyl)-2-(4-(methylsulfonyl)phenyl)-4-H-1-benzopyran-4-one,
6-Fluoro-3-(2-methoxy-5-pyridinyl)-2-(4-(methylsulfonyl)phenyl)-4H-1-benzopyran-4-one,
3-(2-Chloro-5-pyridinyl)-2-(4-(methylsulfonyl)phenyl)-4H-1-benzopyran-4-one,
3-(2-Chloro-5-pyridinyl)-6-fluoro 2-(4-(methylsulfonyl)phenyl)-4H-1-benzopyran-4-one,
3-(2-Fluoro-5-pyridinyl)-2-(4-(methylsulfonyl)phenyl)-4H-1-benzopyran-4-one,
6-fluoro-3-(2fluoro)-5-pyridinyl)-2-(4-(methylsulfonyl)phenyl)-4H-1-benzopyran-4-one,
7-fluoro-3-(2-fluoro)-5-pyridinyl)-2-(4-(methylsulfonyl)phenyl)-4H-1-benzopyran-4-one,
3-(4-Chloro-3-pyridinyl)-2-(4-(methylsulfonyl)phenyl)-4H-1-benzopyran-4-one,
3-(4-Fluorophenyl)-6-methoxy-2-(4-(methylsulfonyl)phenyl)-4H-1-benzopyran-4-one,
2-(4-(Methylsulfonyl)phenyl)-3-(2-trifluoromethyl-5-pyridinyl)-4H-1-benzopyran-4-one,
3-(2-Fluoro-3-pyridinyl)-2-(4-(methylsulfonyl)phenyl)-4H-1-benzopyran-4-one,
3-(2-Chloro-3-pyridinyl)-2-(4-(methylsulfonyl)phenyl)-4H-1-benzopyran-4-one,
3-(5-Bromo-3-pyridinyl)-2-(4-(methylsulfonyl)phenyl)-4H-1-benzopyran-4-one,
3-(2-Furyl)-2-(4-(methylsulfonyl)phenyl)-4H-1-benzopyran-4-one,
3-(5-Indanyl)-2-(4-(methylsulfonyl)phenyl)-4H-1-benzopyran-4-one,
3-(4-Fluorophenyl)-6-methyl-2-(4-(methylsulfonyl)phenyl)-4H-1-benzopyran-4-one,
3-(4-Fluorophenyl)-6-hydroxy-2-(4-(methylsulfonyl)phenyl)-4H-1-benzopyran-4-one,
2-(4-(Aminosulfonyl)phenyl)-3-(2-methylphenyl)-4H-1-benzopyran-4-one,
2-(4-(Aminosulfonyl)phenyl)-3-phenyl-4H-1-benzopyran-4-one,
2-(4-(Aminosulfonyl)phenyl)-3-(3,4difluorophenyl)-4H-1-benzopyran-4-one,
2-(4-(Aminosulfonyl)phenyl)-3-(4-chloro-3-fluorophenyl)-4H-1-benzopyran-4-one,
2-(4-(Aminosulfonyl)phenyl)-3-(3-chloro-4-fluorophenyl)-4H-1-benzopyran-4one,
2-(4-(Aminosulfonyl)phenyl)-3-(3,4dichlorophenyl)-4H-1-benzopyran-4-one,
2-(4-(Aminosulfonyl)phenyl)-3-(2-chlorophenyl)-4H-1-benzopyran-4-one,
2-(4-(Aminosulfonyl)phenyl)-3-(3-chlorophenyl)-4H-1-benzopyran-4-one,
2-(4-(Aminosulfonyl)phenyl)-3-(4-chlorophenyl)-4H-1-benzopyran-4-one,
2-(4-(Aminosulfonyl)phenyl)-3-((4-methylthio)phenyl)-4H-1-benzopyran-4-one,
2-(4-(Aminosulfonyl)phenyl)-3-((3,4-methylenedioxy)phenyl)-4H-1-benzopyran-4-one,
2-(4-(Aminosulfonyl)phenyl)-3-(2,3-difluorophenyl)-4H-1-benzopyran-4-one,
2-(4-(Aminosulfonyl)phenyl)-3-(3-fluorophenyl)-4H-1-benzopyran-4-one,
2-(4-(Aminosulfonyl)phenyl)-3-(2-fluorophenyl)-4H-1-benzopyran-4-one,
2-(4-(Aminosulfonyl)phenyl)-3-(2,4-difluorophenyl)-4H-1-benzopyran-4-one,
2-(4-(Aminosulfonyl)phenyl)-3-(3-methylphenyl)-4H-1-benzopyran-4-one,
2-(4-(Aminosulfonyl)phenyl)-3-(2-methoxyphenyl)-4H-1-benzopyran-4-one,
2-(4-(Aminosulfonyl)phenyl)-6-fluoro-3-(2-fluoro-5-pyridinyl)-4H-1-benzopyran-4-one,
2-(4-(Aminosulfonyl)phenyl)-3-(4-methylphenyl)-4H-1-benzopyran-4-one,
2-(4-(Aminosulfonyl)phenyl)-3-(4-methoxyphenyl)-4H-1-benzopyran-4-one,
2-(4-(Aminosulfonyl)phenyl)-7-fluoro-3-(2-methoxy-5-pyridinyl)-4H-1-benzopyran-4-one,
2-(4-(Aminosulfonyl)phenyl)-3-(3-methoxyphenyl)-4H-1-benzopyran-4-one,
2-(4-(Aminosulfonyl)phenyl)-3-(4-fluorophenyl)-4H-1-benzopyran-4-one,
2-(4-(Aminosulfonyl)phenyl)-3-(2-chloro-5-pyridinyl)-7-fluoro-4H-1-benzopyran-4-one,
2-(4-(Aminosulfonyl)phenyl)-3-(3,5difluorophenyl)-4H-1-benzopyran-4-one,
2-(4-(Aminosulfonyl)phenyl)-3-(2-pyridinyl)-4H-1-benzopyran-4-one,
2-(4-(Aminosulfonyl)phenyl)-3-(3-pyridinyl)-4H-1-benzopyran-4-one,
2-(4-(Aminosulfonyl)phenyl)-6-fluoro-3-(3-pyridinyl)-4H-1-benzopyran-4-one,
2-(4-(Aminosulfonyl)phenyl)-7-fluoro-3-(3-pyridinyl)-4H-1-benzopyran-4-one,
2-(4-(Aminosulfonyl)phenyl)-3-(2-chloro-5-pyridinyl)-4H-1-benzopyran-4-one,
2-(4-(Aminosulfonyl)phenyl)-3-(2-chloro-5-pyridinyl)-6-fluoro-4H-1-benzopyran-4-one,
2-(4-(Aminosulfonyl)phenyl)-3-(2-fluoro-5-pyridinyl)-4H-1-benzopyran-4-one,
2-(4-(Aminosulfonyl)phenyl)-7-fluoro-3-(2-fluoro-5-pyridinyl)-4H-1-benzopyran-4-one,
2-(4-(Aminosulfonyl)phenyl)-3-(2-methyl-5-pyridinyl)-4H-1-benzopyran-4-one,
2-(4-(Aminosulfonyl)phenyl)-3-(2-methoxy-5-pyridinyl)-4H-1-benzopyran-4-one,
2-(4-(Aminosulfonyl)phenyl)-6-fluoro-3-(2-methoxy-5-pyridinyl)-4H-1-benzopyran-4-one, 2-(4-(Aminosulfonyl)phenyl)-3-(4-pyridinyl)-4H-1-benzopyran-4-one,
2-(4-(Aminosulfonyl)phenyl)-3-(2-thienyl)-4H-1-benzopyran-4-one,
2-(4-(Aminosulfonyl)phenyl)-3-(2-furyl)-4H-1-benzopyran-4-one,
2-(4-(Aminosulfonyl)phenyl)-6-fluoro-3-(4fluorophenyl)-4H-1-benzopyran-4-one,
2-(4-(Aminosulfonyl)phenyl)-6-fluoro-3-phenyl-4H-1-benzopyran-4-one,
2-(4-(Aminosulfonyl)phenyl)-6-fluoro-3-(4methylphenyl)-4H-1-benzopyran-4-one,
2-(4-(Aminosulfonyl)phenyl)-6-fluoro-3-(4-chlorophenyl)-4H-1-benzopyran-4-one,
2-(4-(Aminosulfonyl)phenyl)-6-fluoro-3-(3-fluorophenyl)-4H-1-benzopyran-4-one,
2-(4-(Aminosulfonyl)phenyl)-7-fluoro-3-(4-fluorophenyl)-4H-1-benzopyran-4-one,
2-(4-(Aminosulfonyl)phenyl)-7-fluoro-3-(3-fluorophenyl)-4H-1-benzopyran-4-one,
2-(4-(Aminosulfonyl)phenyl)-7-fluoro-3-(2-fluorophenyl)-4H-1-benzopyran-4-one,
2-(4-(Aminosulfonyl)phenyl)-7-fluoro-3-(3,4-dichlorophenyl)-4H-1-benzopyran-4-one,
2-(4-(Aminosulfonyl)phenyl)-8-chloro-3-(4-fluorophenyl)-5-hydroxy-4H-1-benzopyran-4-one,
2-(4-(Aminosulfonyl)phenyl)-8-chloro-3-(4-fluorophenyl)-5-methoxy-4H-1-benzopyran-4-one,
2-(4-(Aminosulfonyl)phenyl)-6-methoxy-3-(4-fluorophenyl)-4H-1-benzopyran-4-one,
2-(4-(Aminosulfonyl)phenyl)-7-methoxy-3-(4-fluorophenyl)-4H-1-benzopyran-4-one,
2-(4-(Aminosulfonyl)phenyl)-6-hydroxy-3-(4-fluorophenyl)-4H-1-benzopyran-4-one,
2-(4-(Methylsulfonyl)phenyl)-3-phenyl-4H-1-benzopyran-4-thione,
3-(4-Fluorophenyl)-2-(4-(methylsulfonyl)phenyl)-4H-1-benzopyran-4-thione,
6-Fluoro-3-(4-fluorophenyl)-2-(4-(methylsulfonyl)phenyl)-4H-1-benzopyran-4-thione,
3-(2-Fluorophenyl)-2-(4-(methylsulfonyl)phenyl)-4H-1-benzopyran-4-thione,
7-Fluoro-2-(4-(methylsulfonyl)phenyl)-3-(3-pyridinyl)-4H-1-benzopyran-4-thione,
3-(3-Fluorophenyl)-2-(4-(methylsulfonyl)phenyl)-4H-1-benzopyran-4-thione,
3-(2-Methylphenyl)-2-(4-(methylsulfonyl)phenyl)-4H-1-benzopyran-4-thione,
3-(4-Methylphenyl)-2-(4-(methylsulfonyl)phenyl)-4H-1-benzopyran-4-thione,
3-(3-Methylphenyl)-2-(4-(methylsulfonyl)phenyl)-4H-1-benzopyran-4-thione,
3-(4-Methoxyphenyl)-2-(4-(methylsulfonyl)phenyl)-4H-1-benzopyran-4-thione,
6-Fluoro-2-(4-(methylsulfonyl)phenyl)-3-(3-pyridinyl)-4H-1-benzopyran-4-thione,
3-(2-Chlorophenyl)-2-(4-(methylsulfonyl)phenyl)-4H-1-benzopyran-4-thione,
3-(2,3-Dichlorophenyl)-2-(4-(methylsulfonyl)phenyl)4H-1-benzopyran-4-thione,
3-(3,4-Dichlorophenyl)-2-(4-(methylsulfonyl)phenyl)-4H-1-benzopyran-4-thione,
3-(3-Chlorophenyl)-2-(4-(methylsulfonyl)phenyl)-4H-1-benzopyran-4-thione,
3-(4-Chlorophenyl)-2-(4-(methylsulfonyl)phenyl)-4H-1-benzopyran-4-thione,
3-(3-Methoxyphenyl)-2-(4-(methylsulfonyl)phenyl)-4H-1-benzopyran-4-thione,
2-(4-(Methylsulfonyl)phenyl)-3-(4-trifluoromethylphenyl)-4H-1-benzopyran-4-thione,
3-(3-Chloro-4-fluorophenyl)-2-(4-(methylsulfonyl)phenyl)-4H-1-benzopyran-4-thione,
2-(4-(Methylsulfonyl)phenyl)-3-(3-pyridinyl)-4H-1-benzopyran-4-thione,
2-(4-(Aminosulfonyl)phenyl)-6-fluoro-3-(3-pyridinyl)-4H-1-benzopyran-4-thione,
2-(4-(Aminosulfonyl)phenyl)-3-(3-pyridinyl)-4H-1-benzopyran-4-thione,
2-(4-(Aminosulfonyl)phenyl)-3-(4-fluorophenyl)-4H-1-benzopyran-4-thione,
2-(4-(Aminosulfonyl)phenyl)-3-(2-fluorophenyl)-4H-1-benzopyran-4-thione,
2-(4-(Aminosulfonyl)phenyl)-3-(4-chlorophenyl)-4H-1-benzopyran-4-thione,
2-(4-(Aminosulfonyl)phenyl)-3-phenyl-4H-1-benzopyran-4-thione,
2-(4-(Aminosulfonyl)phenyl)-6-fluoro-3-(4-fluorophenyl)-4H-1-benzopyran-4-thione, or
2-(4-(Aminosulfonyl)phenyl)-7-fluoro-3-(3-pyridinyl)-4H-1-benzopyran-4-thione.

3. The compound (1) according to claim 1, which is
2-(4-(Methylsulfonyl)phenyl)-3-phenyl-4H-1-benzopyran-4-one,
3-(4-Fluorophenyl)-2-(4-(methylsulfonyl)phenyl)-4H-1-benzopyran-4-one,
2-(4-(Methylsulfonyl)phenyl)-3-(4-trifluoromethylphenyl)-4H-1-benzopyran-4-one,
3-(4-Methylphenyl)-2-(4-(methylsulfonyl)phenyl)-4H-1-benzopyran-4-one,
3-(2,4-Dichlorophenyl)-2-(4-(methylsulfonyl)phenyl)-4H-1-benzopyran-4-one,
3-(4-Acetylphenyl)-2-(4-(methylsulfonyl)phenyl)-4H-1-benzopyran-4-one,
3-(4-Formylphenyl)-2-(4-(methylsulfonyl)phenyl)-4H-1-benzopyran-4-one,
3-(4-Methoxyphenyl)-2-(4-(methylsulfonyl)phenyl)-4H-1-benzopyran-4-one,
3(3,4-Dichlorophenyl)-2-(4-(methylsulfonyl)phenyl)-4H-1-benzopyran-4-one,
3-(2-Fluorophenyl)-2-(4-(methylsulfonyl)phenyl)-4H-1-benzopyran-4-one,
3-(3,5-Dichlorophenyl)-2-(4-(methylsulfonyl)phenyl)-4H-1-benzopyran-4-one,
3-(N-methyl-3-pyrazolyl)-2-(4-(methylsulfonyl)phenyl)-4H-1-benzopyran-4-one,
3-(4-Chlorophenyl)-2-(4-(methylsulfonyl)phenyl)-4H-1-benzopyran-4-one,
2-(4-(Methylsulfonyl)phenyl)-3-(3-nitrophenyl)-4H-1-benzopyran-4-one,
2-(4-(Methylsulfonyl)phenyl)-3-(1-naphthyl)-4H-1-benzopyran-4-one,
3-(3-Methylphenyl)-2-(4-(methylsulfonyl)phenyl)-4H-1-benzopyran-4-one,
3-(2-Methylphenyl)-2-(4-(methylsulfonyl)phenyl)-4H-1-benzopyran-4-one,
3-(3-Chloro-4-fluorophenyl)-2-(4-(methylsulfonyl)phenyl)-4H-1-benzopyran-4-one,
3-(4-Bromophenyl)-2-(4-(methylsulfonyl)phenyl)-4H-1-benzopyran-4-one,
3-(2,3-Dichlorophenyl)-2-(4-(methylsulfonyl)phenyl)-4H-1-benzopyran-4-one,
3-(3-Fluorophenyl)-2-(4-(methylsulfonyl)phenyl)-4H-1-benzopyran-4-one,
3-(3-Chlorophenyl)-2-(4-(methylsulfonyl)phenyl)-4H-1-benzopyran-4-one, 3-(2-Benzo[b]thienyl)-2-(4-(methylsulfonyl)phenyl)-4H-1-benzopyran-4-one,
2-(4-(Methylsulfonyl)phenyl)-3-(2-pyridinyl)-4H-1-benzopyran-4-one,
2-(4-(Methylsulfonyl)phenyl)-3-(3-pyridinyl)-4H-1-benzopyran-4-one,
2-(4-(Methylsulfonyl)phenyl)-3-(4-pyridinyl)-4H-1-benzopyran-4-one,
6-Fluoro-2-(4-(methylsulfonyl)phenyl)-3-(3-pyridinyl)-4H-1-benzopyran-4-one,
2-(4-(Methylsulfonyl)phenyl)-3-(2-thienyl)-4-1-benzopyran-4-one,
3-(2-Methyl-5-pyridinyl)-2-(4-(methylsulfonyl)phenyl)-4H-1-benzopyran-4-one,
3-(2-Methoxy-5-pyridinyl)-2-(4-(methylsulfonyl)phenyl)-4H-1-benzopyran-4-one,
6-Fluoro-3-(2-methyl-5-pyridinyl)-2-(4-(methylsulfonyl)phenyl)-4H-1-benzopyran-4-one,
3-(2-Chloro-5-pyridinyl)-2-(4-(methylsulfonyl)phenyl)-4H-1-benzopyran-4-one,
3-(4-Chloro-3-pyridinyl)-2-(4-(methylsulfonyl)phenyl)-4H-1-benzopyran-4-one,
2-(4-(Methylsulfonyl)phenyl)-3-(2-trifluoromethyl-5-pyridinyl)-4H-1-benzopyran-4-one,
3-(5-Bromo-3-pyridinyl)-2-(4-(methylsulfonyl)phenyl)-4H-1-benzopyran-4-one,
2-(4-(Aminosulfonyl)phenyl)-3-phenyl-4H-1-benzopyran-4-one,
2-(4-(Aminosulfonyl)phenyl)-3-(3,4-dichlorophenyl)-4H-1-benzopyran-4-one,
2-(4-(Aminosulfonyl)phenyl)-3-((4-methylthio)phenyl)-4H-1-benzopyran-4-one,
2-(4-(Aminosulfonyl)phenyl)-3-((3,4-methylenedioxy)phenyl)-4H-1-benzopyran4-one,
2-(4-(Aminosulfonyl)phenyl)-3-(2-fluorophenyl)-4H-1-benzopyran-4-one,
2-(4-(Aminosulfonyl)phenyl)-3-(4-methoxyphenyl)-4H-1-benzopyran-4-one,
2-(4-(Aminosulfonyl)phenyl)-3-(4-fluorophenyl)-4H-1-benzopyran-4-one,
2-(4-(Aminosulfonyl)phenyl)-6-fluoro-3-(4-fluorophenyl)-4H-1-benzopyran-4-one,
2-(4-(Aminosulfonyl)phenyl)-6-fluoro-3-phenyl-4H-1-benzopyran-4-one,
2-(4-(Aminosulfonyl)phenyl)-6-fluoro-3-(4-methylphenyl)-4H-1-benzopyran-4-one,
2-(4-(Aminosulfonyl)phenyl)-6-fluoro-3-(4-chlorophenyl)-4H-1-benzopyran-4-one,
2-(4-(Aminosulfonyl)phenyl)-6-fluoro-3-(3-fluorophenyl)-4H-1-benzopyran-4-one,
2-(4-(Aminosulfonyl)phenyl)-7-fluoro-3-(4-fluorophenyl)-4H-1-benzopyran-4-one,
2-(4-(Aminosulfonyl)phenyl)-7-fluoro-3-(3-fluorophenyl)-4H-1-benzopyran-4-one,
2-(4-(Aminosulfonyl)phenyl)-7-fluoro-3-(2-fluorophenyl)-4H-1-benzopyran-4-one,
2-(4-(Aminosulfonyl)phenyl)-7-fluoro-3-(3,4-dichlorophenyl)-4-H-1-benzopyran-4-one,
2-(4-(Aminosulfonyl)phenyl)-8-chloro-3-(4-fluorophenyl)-5-hydroxy-4H-1-benzopyran-4-one,
2-(4-(Aminosulfonyl)phenyl)-8-chloro-3-(4-fluorophenyl)-5-methoxy-4H-1
2-(4-(Aminosulfonyl)phenyl)-6-methoxy-3-(4-fluorophenyl)-4H-1-benzopyran-4-one,
2-(4-(Aminosulfonyl)phenyl)-7-methoxy-3-(4-fluorophenyl)-4H-1-benzopyran-4-one,
2-(4-(Aminosulfonyl)phenyl)-6-hydroxy-3-(4-fluorophenyl)-4H-1-benzopyran-4-one,
2-(4-(Methylsulfonyl)phenyl)-3-phenyl-4H-1-benzopyran-4-thione,
3-(4-Fluorophenyl)-2-(4-(methylsulfonyl)phenyl)-4H-1-benzopyran-4-thione,
3-(2-Fluorophenyl)-2-(4-(methylsulfonyl)phenyl)-4H-1-benzopyran-4-thione,
3-(3-Fluorophenyl)-2-(4-(methylsulfonyl)phenyl)-4H-1-benzopyran-4-thione,
3-(2-Methylphenyl)-2-(4-(methylsulfonyl)phenyl)-4H-1-benzopyran-4-thione,
3-(4-Methylphenyl)-2-(4-(methylsulfonyl)phenyl)-4H-1-benzopyran-4-thione,
3-(3-Methylphenyl)-2-(4-(methylsulfonyl)phenyl)-4H-1-benzopyran-4-thione,
3-(4-Methoxyphenyl)-2-(4-(methylsulfonyl)phenyl)-4H-1-benzopyran-4-thione,
3-(2,3-Dichlorophenyl)-2-(4-(methylsulfonyl)phenyl)-4H-1-benzopyran-4-thione,
3-(3,4-Dichlorophenyl)-2-(4-(methylsulfonyl)phenyl)-4H-1-benzopyran-4-thione,
3(3-Chlorophenyl)-2-(4-(methylsulfonyl)phenyl)-4H-1-benzopyran-4-thione,
2-(4-(Aminosulfonyl)phenyl)-3-(4-fluorophenyl)-4H-1-benzopyran-4-thione, or
2-(4-(Aminosulfonyl)phenyl)-6-fluoro-3-(4-fluorophenyl)-4H-1-benzopyran-4-thione.

4. A pharmaceutical composition for treating an inflammation, which comprises a therapeutically effective amount of a compound or a pharmaceutically acceptable salt thereof of any one of claims 1, 2 or 3 and a pharmaceutically acceptable carrier.

5. A pharmaceutical composition for treating a cyclooxygenase-2mediated disease, which comprises a therapeutically effective amount of compound or a pharmaceutically acceptable salt thereof of any one of claims 1, 2 or 3 and a pharmaceutically acceptable carrier.

6. A pharmaceutical composition for treating a disease susceptible to nonsteroidal anti-inflammatory drugs, which comprises a therapeutically effective amount of a compound or a pharmaceutically acceptable salt thereof of any one of claims 1, 2 or 3 and a pharmaceutically acceptable carrier.

* * * * *